US009057051B2

(12) United States Patent
Pauwelyn et al.

(10) Patent No.: US 9,057,051 B2
(45) Date of Patent: Jun. 16, 2015

(54) OPTIMIZED METHODS FOR DIFFERENTIATION OF CELLS INTO CELLS WITH HEPATOCYTE PROGENITOR PHENOTYPES, CELLS PRODUCED BY THE METHODS, AND METHODS OF USING THE CELLS

(75) Inventors: Karen Pauwelyn, Hechtel Eksel (BE); Catherine M. Verfaillie, Leuven (BE)

(73) Assignee: KATHOLIEKE UNIVERSITEIT LEUVEN, Leuven (BE)

( * ) Notice: Subject to any disclaimer, the term of this patent is extended or adjusted under 35 U.S.C. 154(b) by 598 days.

(21) Appl. No.: 13/126,834

(22) PCT Filed: Oct. 31, 2008

(86) PCT No.: PCT/IB2008/003868
§ 371 (c)(1),
(2), (4) Date: Aug. 12, 2011

(87) PCT Pub. No.: WO2010/049752
PCT Pub. Date: May 6, 2010

(65) Prior Publication Data
US 2011/0287539 A1    Nov. 24, 2011

(51) Int. Cl.
  *A61K 38/00* (2006.01)
  *A61K 35/12* (2006.01)
  *C12N 5/0735* (2010.01)
  *C12N 5/071* (2010.01)
  *C12N 5/074* (2010.01)

(52) U.S. Cl.
  CPC .............. *C12N 5/0606* (2013.01); *C12N 5/067* (2013.01); *C12N 2501/113* (2013.01); *C12N 2501/115* (2013.01); *C12N 2501/119* (2013.01); *C12N 2501/12* (2013.01); *C12N 2501/155* (2013.01); *C12N 2501/16* (2013.01); *C12N 2501/415* (2013.01); *C12N 2506/02* (2013.01); *C12N 2506/03* (2013.01); *C12N 5/0696* (2013.01)

(58) Field of Classification Search
  CPC .............................. A61K 38/00; A61K 35/12
  USPC ................................................ 435/325, 377
  See application file for complete search history.

(56) References Cited

U.S. PATENT DOCUMENTS

| 5,486,359 | A |   | 1/1996 | Caplan et al. |
| 5,827,735 | A |   | 10/1998 | Young et al. |
| 5,906,934 | A |   | 5/1999 | Grande et al. |
| 5,942,435 | A | * | 8/1999 | Wheeler ......................... 435/325 |
| 6,090,625 | A |   | 7/2000 | Abuljadayel |
| 6,214,369 | B1 |  | 4/2001 | Grande et al. |
| 6,653,134 | B2 |  | 11/2003 | Prockop et al. |
| 6,777,231 | B1 |  | 8/2004 | Katz et al. |
| 7,045,148 | B2 |  | 5/2006 | Hariri |
| 7,056,738 | B2 |  | 6/2006 | Prockop et al. |
| 7,229,827 | B2 |  | 6/2007 | Kim et al. |
| 7,311,905 | B2 |  | 12/2007 | Hariri |
| 2001/0033834 | A1 | 10/2001 | Wilkison et al. |
| 2001/0046489 | A1 | 11/2001 | Habener et al. |
| 2002/0061587 | A1 | 5/2002 | Anversa |
| 2002/0164794 | A1 | 11/2002 | Wernet |
| 2003/0003090 | A1 | 1/2003 | Prockop et al. |
| 2003/0032179 | A1 | 2/2003 | Hariri |
| 2003/0059414 | A1 | 3/2003 | Ho et al. |
| 2004/0033214 | A1 | 2/2004 | Young et al. |
| 2004/0235165 | A1 | 11/2004 | Prockop et al. |
| 2005/0152995 | A1 | 7/2005 | Chen |
| 2005/0169896 | A1 | 8/2005 | Li et al. |
| 2005/0255588 | A1 | 11/2005 | Young et al. |
| 2006/0177925 | A1 | 8/2006 | Rosenberg et al. |
| 2006/0286544 | A1 | 12/2006 | Mandal et al. |
| 2007/0010484 | A1 | 1/2007 | Schwartz |
| 2007/0104697 | A1 | 5/2007 | Wilkison |
| 2008/0181865 | A1 | 7/2008 | Schaebitz |
| 2008/0248567 | A1 | 10/2008 | Singla |
| 2010/0239542 | A1 | 9/2010 | Young et al. |
| 2010/0239543 | A1 | 9/2010 | Young et al. |
| 2011/0064701 | A1 | 3/2011 | Young et al. |

FOREIGN PATENT DOCUMENTS

| WO | WO 96/23870 | 8/1996 |
| WO | WO 99/16863 | 4/1999 |
| WO | WO 99/35243 | 7/1999 |
| WO | WO 01/04268 | 1/2001 |

(Continued)

OTHER PUBLICATIONS

Soto-Guitterz et al., 2006, Nature Biotechnology, vol. 24(1), pp. 1412-1419.*
Latella et al. (2000, Cell Death and Differentiation, vol. 7, pp. 145-154).*
D'Amour et al. (2005, Nature Biotechnology, vol. 23(2), pp. 1534-1541).*
Brevini et al., 2010, Theriogenology, vol. 74, pp. 544-550.*
Paris et al. (2010, Theriogenology, vol. 74, pp. 516-524).*
Munoz et al. (2008, Theriogenology, vol. 69, pp. 1159-1164).*
Petitte et al. (2004, Mech. of Develop., vol. 121, pp. 1159-1168).*
Lavial et al. (2010, Develop. Growth Diff., vol. 52, pp. 101-114).*
Liu et al. (2004, Experimental Neurology, vol. 190, pp. 109-121).*
Kosaka et al. (2006, FASEB J., vol. 20, pp. E623-E629).*

(Continued)

*Primary Examiner* — Anoop Singh
*Assistant Examiner* — David A Montanari
(74) *Attorney, Agent, or Firm* — Tarolli, Sundheim, Covell & Tummino LLP

(57) ABSTRACT

The invention is directed to methods for culturing cells so that the cells are induced to differentiate into cells that express hepatocyte phenotypes and hepatocyte progenitor phenotypes. More particularly, the invention relates to methods for culturing cells so that the cells are induced to differentiate into cells that express a definitive endodermal phenotype, a liver-committed endodermal phenotype, a hepatoblast phenotype, and hepatocyte phenotype. The invention is also directed to cells produced by the methods of the invention. The cells are useful, among other things, for treatment of liver deficiency, liver metabolism studies, and liver toxicity studies.

10 Claims, 14 Drawing Sheets

(56) References Cited

FOREIGN PATENT DOCUMENTS

| WO | WO 01/08691 | 2/2001 |
|---|---|---|
| WO | WO 01/21766 | 3/2001 |
| WO | WO 01/21767 | 3/2001 |
| WO | WO 02/08388 | 3/2001 |
| WO | WO 01/62901 | 8/2001 |
| WO | WO 02/34890 | 5/2002 |
| WO | WO 2004/087896 | 10/2004 |

OTHER PUBLICATIONS

Kubo et al. (2004, Development, vol. 131, pp. 1651-1662).*
Cambrex specimens, "Poietics Human Mesenchymal Stem Cell Systems," Cambrex BioScience Walkersville, Inc. (2005).
Prockop, D., "Marrow stromal cells as stem cells for nonhematopoietic tissues" Science; 276:71-74 (1997).
Bjornson et al., "Turning brain into blood: a hematopoietic fate adopted by adult neural stem cells in vivo" Science; 283:534-537 (1999).
Reyes et al., "Purification and ex vivo expansion of postnatal human marrow mesodermal progenitor cells" Blood; 98:2615-25 (2001).
Bouwens, L., "Transdifferentiation versus stem cell hypothesis for the regeneration of islet beta-cells in the pancreas" Microscopy Research and Technique; 43:332-336 (1998).
Reyes et al., "Origin of endothelial progenitors in human postnatal bone marrow" J. Clin. Invest.; 109:1-10 (2002).
Reyes at al., "Characterization of multilineage mesodermal progenitor cells in adult marrow" Abstract No. 124, American Society for Hematology (2001).
Reyes at al., "Turning marrow into brain: generation of glial and neuronal cells from adult bone marrow mesenchymal stem cells" Abstract No. 1676, American Society for Hematology (2001).
Reyes et al., "Skeletal smooth and cardiac muscle differentiation from single adult marrow derived mesodermal progenitor cells" Abstract No. 2610, American Society for Hematology (2001).
Reyes et al., "In vitro and in vivo characterization of neural cells derived from mesenchymal stem cells" Abstract 2126, American Society for Hematology (2001).
Reyes et al., "Endothelial cells generated from human marrow derived mesenchymal stem cells (MSC)" Abstract No. 2276, American Society for Hematology (2001).
Zhao et al., "Immunohistochemical identification of multipotent adult progenitor cells from human bone marrow after transplantation into the rat brain" Brain Res Brain Res Protoc; 11:38-45 (2003).
Jiang et al., "Multipotent progenitor cells can be isolated from postnatal murine bone marrow, muscle, and brain" Exp. Hematol.; 30:896-904 (2002).
Jiang et al., "Pluripotency of mesenchymal stem cells derived from adult marrow" Nature; 418:41-49 (2002).
Schwartz, R., "Multipotent adult progenitor cells from bone marrow differentiate into hepatocyte-like cells" J Clin Invest.; 109:1291-1302 (2002).
Zhao et al., "Human bone marrow stem cells exhibit neural phenotypes and ameliorate neurological deficits after grafting into the ischemic brain of rats" Exp Neurol; 174:11-20 (2002).
Lamming et al., "Spontaneous circulation of myeloid-lymphoid-initiating cells and SCID-repopulating cells in sickle cell crisis" J. Clin. Invest.; 111:811-819 (2003).
Qi et al., "Identification of genes responsible for osteoblast differentiation from human mesodermal progenitor cells" Nat. Acad. Sci. USA; 100:3305-3310 (2003).
Verfaillie, C. "Investigator Profile" Journal of Hematotherapy and Stem Cell Research; 11:441-444 (2002).
Verfaillie et al., "Stem cells: hype and reality" Hematology (Am Soc Hematol Educ Program); 369-391 (2002).
Verfaille, C., "Optimizing hematopoietic stem cell engraftment: a novel role for thrombopoeitin" J. Clin. Invest.; 110:303-304 (2002).
Liu et al., "Myeloid-lymphoid-initiating cells (ML-IC) are highly enriched in the rhodamine-C-Kit(+) CD33(−)CD38(−) fraction of umbilical cord CD34(+)" Exp. Hematol.; 30:582-589 (2002).
Lewis at al., "Multi-lineage expansion potential of primitive hematopoietic progenitors: superiority of umbilical cord blood compared to mobilized peripheral blood" Exp. Hematol.; 28:1087-1095 (2002).
Verfaillie, C.M., "Meeting Report on an NHLBI Workshop on ex vivo expansion of stem cells, Jul. 29, 1999, Washington D.C. National Heart Lung and Blood Institute" Exp. Hematol.; 28:361-364 (2000).
Punzel et al., "The myeloid-lymphoid initiating cell (ML-IC) assay assesses the fate of multipotent human progenitors in vitro" Blood; 93:3750-3756 (1999).
Roy at al., "Expression and function of cell adhesion molecules on fetal liver, cord blood and bone marrow hematopoietic progenitors: implications for anatomical localization and developmental stage specific regulation of hematopoiesis" Exp. Hematol.; 27:302-312 (1999).
Miller et al., "Ex vivo culture of CD34+/Lin-/DR- cells in stroma-derived soluble factors, interleukin-3, and macrophage inflammatory protein-1 alpha maintains not only myeloid but also lymphoid progenitors in a novel switch culture assay" Blood; 15:4516-4522 (1998).
Verfaillie, C., "Stem cells in chronic myelogenous Leukemia" Hematol. Oncol. Clin. North Am.; 11:1079-1114 (1997).
Prosper et al., "Phenotypic and functional characterization of long-term culture-initiating cells present in peripheral blood progenitor collections of normal donors treated with granulocyte colony-stimulating factor" Blood; 15:2033-2042 (1996).
Lodie et al., "Systematic analysis of reportedly distinct populations of multipotent bone marrow-derived stem cells reveals a lack of distinction" Tissue Engineering; 8:739-751 (2002).
Pagen Westphal, S., "Adult bone marrow eyed as source of stem cells" Boston Globe, Jan. 24, 2002.
Pagen Westphal, S., "Ultimate stem cell discovered" New Scientist, Jan. 23, 2002.
Wade et al., "Scientists herald a versatile adult cell" The New York Times on the Web, Jan. 25, 2002.
Rosford et al, "The octamer motif present in the Rex-1 promoter binds Oct-1 and Oct-3 expressed by EC cells and ES cells" Biochem. Biophys. Res. Comm.; 203:1795-1802 (1994).
Rosner et al., "Oct-3 is a maternal factor required for the first mouse embryonic division" Cell; 64:1103-1110 (1991).
Pittenger et al., "Multilineage potential of adult human mesenchymal stem cells"; Science; 284:143-147 (1999).
Ben-Shushan et al., "Rex1, a gene encoding a transcription factor expressed in the early embryo, is regulated via Oct-3/4 and Oct-6 binding to and octamer site and a novel protein, R ox-1, binding to an adjacent site" Mol. Cell Biol.; 18:1866-1878 (1998).
Reyes et al., "Characterization of multipotent adult progenitor cells, a subpopulation of mesenchymal stem cells" Annals of the New York Academy of Science; 938:231-235 (2001).
Anjos-Afonso and Bonnet, "Nonhematopoietic/endothelial SSE-1+ cells define the most primitive progenitors in the adult murine bone marrow mesenchymal compartment" Blood; 109:1298-1306 (2007).
Bertani et al., "Neurogenic potential of human mesenchymal stem cells revisited: analysis by immunostaining, time-lapse video and microarray" J Cell Sci.; 118:3925-36 (2005).
Bodnar et al., "Extension of life-span by introduction of telomerase into normal human cells" Science; 279:349-352 (1998).
Horwitz et al., "Clarification of the nomenclature for MSC: The international society for cellular therapy position paper" Cytotherapy; 7:393-395 (2005).
Lu et al., "Induction of bone marrow stromal cells to neurons: differentiation, transdifferentiation, or artifact" J Neurosci Res; 77:174-91 (2004).
Neuhuber et al., "Reevaluation of in vitro differentiation protocols for bone marrow stromal cells: disruption of actin cytoskeleton induces rapid morphological changes and mimics neuronal phenotype" J Neurosci Res; 77:192-204 (2004).
Simonsen et al., "Telomerase expression extends the proliferative life-span and maintains the osteogenic potential of human bone marrow stromal cells" Nature Biotechnology; 20:592-596 (2002).
Zimmerman et al., "Lack of telomerase activity in human mesenchymal stem cells" Leukemia; 17:1146-1149 (2003).

(56) References Cited

OTHER PUBLICATIONS

Izadpanah et al., "Biologic properties of mesenchymal stem cells derived from bone marrow and adipose tissue" Journal of Cellular Biochemistry; 99:1285-1297 (2006).
Long et al., "Neural cell differentiation in vitro from adult human bone marrow mesenchymal stem cells" Stem Cells and Development; 14:65-69 (2005).
Moriscot et al., "Human bone marrow mesenchymal stem cell can express insulin and key transcription factors of the endocrine pancreas developmental pathway upon genetic and/or microenvironmental manipulation in vitro" Stem Cells; 23:594-604 (2005).
Sanchez-Ramos et al., "Adult bone m arrow stromal cells differentiate into neural cells in vitro" Exp. Neural.; 164:247-56 (2000).
Eglitis at al., "Hematopoietic cells differentiate into both microglia and macroglia in the brain of adult mice" Proc. Natl. Acad. Sci. USA; 94:4080-85 (1997).
Kopen at al., "Marrow stromal cells migrate throughout forebrain and cerebellum, and they differentiate into astrocytes after injection into neonatal mouse brains" Proc. Natl. Acad. Sci. USA; 96:10711-16 (1999).
Lagasse at al., "Purified hematopoietic stem cells can differentiate into hepatocytes in vivo" Nature Medicine; 6:1229-1234 (2000).
Wang, X. et al., "Cell fusion is the principal source of bone-marrow-derived hepatocytes" Nature; 422:897-901 (2003).
Giles, J., "The trouble with replication" Nature, 422:344-347 (2006).
Verfaillie, C.M., Multipotent adult progenitor cells: an update: Novartis Found Symp., 254:55-65 (2005).
Aldhous et al., "Fresh questions on stem cell findings" New Scientist, Mar. 21, 2007.
Brazelton et al., "From marrow to brain: expression of neuronal phenotypes in adult mice" Science; 290:1775-9 (2000).
Clarke et al., "Generalized potential of adult neural stem cells" Science; 288: 1660-3 (2000).
Johansson at al., "Neural stem cells in the adult human brain" Exp. Cell. Res.; 253:733-6 (1999).
Mezey et al., "Turning blood into brain: cells bearing neuronal antigens generated in vivo from bone marrow" Science; 290:1779-82 (2000).
Morshead et al., "Hematopoietic competence is a rare property of neural stem cells that may depend on genetic and epigenetic alterations" Nat. Med.; 8:268-73 (2002).
Petersen et al., "Bone marrow as a potential source of hepatic oval cells" Science; 284:1168-70 (1999).
Scintu et al., "Differentiation of human bone marrow stem cells into cells with a neural phenotype: diverse effects of two specific treatments" BMC Neurosci.; 7:14 (2006).
U.S. Patent and Trademark Office, Office Action dated Jun. 24, 2005 in related U.S. Appl. No. 10/040,757.
U.S. Patent and Trademark Office, Office Action and 892 dated Jun. 27, 2008 in related U.S. Appl. No. 10/467,963.
U.S. Patent and Trademark Office, Office Action dated Oct. 15, 2009 in related U.S. Appl. No. 10/467,963.
U.S. Patent and Trademark Office, Office Action and 892 dated Apr. 7, 2008 in related U.S. Appl. No. 11/151,689.
U.S. Patent and Trademark Office, Office Action dated Jan. 4, 2006 in related U.S. Appl. No. 11/238,234.
U.S. Patent and Trademark Office, Office Action dated Aug. 29, 2006 in related U.S. Appl. No. 11/238,234.
U.S. Patent and Trademark Office, Office Action and 892 dated Apr. 3, 2007 in related U.S. Appl. No. 11/238,234.
U.S. Patent and Trademark Office, Office Action dated Oct. 7, 2008 in related U.S. Appl. No. 11/238,234.
Communication and 1449, filed Oct. 2, 2007 in related U.S. Appl. No. 11/238,234, and supplemental 1449 submitted on Oct. 4, 2007.
Information Disclosure Statement, Second Communication and PTO/SB/08b, filed Dec. 24, 2008 in related U.S. Appl. No. 11/238,234.
Yuan et al., Dev Neurosci 25:72-78 (2003).
International Search Report for PCT/IB2008/003868.
Flaim, C. et al., "Combinatorial signaling microenvironments for studying stem cell fate" Stem Cells and Development (2008).
Tsuchida, K., Activins, Myostatin and Related TGF-β Family Members as Novel Therapeutic Targets for Endocrine, Metabolic and Immune Disorders (2004).
Endo, D., et al. "Activin or Follistatin: Which is More Beneficial to Support Liver Regeneration After Massive Hepatectomy?" (2006).
Albano, R., et al., Follistatin expression in ES and F9 cells and in preimplantation mouse embryos: (1994).
Decision on Motions; Patent Interference No, 105.953 SGL, Tech Center 1600; filed Sep. 26, 2014.

* cited by examiner

Time dependent increase of albumin concentration during hepatic differentiation of rMAPC-1 (mean of >10 experiments).

US 9,057,051 B2

OPTIMIZED METHODS FOR DIFFERENTIATION OF CELLS INTO CELLS WITH HEPATOCYTE PROGENITOR PHENOTYPES, CELLS PRODUCED BY THE METHODS, AND METHODS OF USING THE CELLS

FIELD OF THE INVENTION

The invention is directed to methods for culturing cells so that the cells are induced to differentiate into cells that express a hepatocyte phenotype and/or hepatocyte progenitor phenotype. More particularly, the invention relates to methods for culturing cells so that the cells are induced to differentiate into cells that express a definitive endodermal phenotype, a liver-committed endodermal phenotype, a hepatoblast phenotype, and hepatocyte phenotype. The invention is also directed to cells produced by the methods of the invention. The cells are useful, among other things, for treatment of liver deficiency, liver metabolism studies, and liver toxicity studies.

BACKGROUND OF THE INVENTION

Liver failure remains a devastating syndrome resulting from the loss of hepatic cell mass below a critical level. Although the prognosis of patients is greatly improved by orthotopic liver transplantation, treatment is limited by worldwide shortages of donor organs. In order to overcome these problems, alternative approaches, such as bio-artificial liver devices, albumin dialysis and cellular based therapy are being evaluated. In recent years, the feasibility to repopulate the liver with different cell types, such as mature and fetal hepatocytes, embryonic stem cells, intrahepatic progenitor cells and bone marrow derived cells, have been assessed in various animal models of liver disease.

Liver Development

Mouse embryonic and fetal liver development can be divided into different consecutive steps. During gastrulation (ED6-ED6.5), future definitive endodermal and mesodermal cells migrate through the primitive streak, located at the prospective posterior and proximal-lateral pole of the embryo. First, anterior endodermal cells ingress the primitive streak, migrate towards the distal tip of the epiblast cup and displace the visceral endoderm. The mesoderm migrates between the epiblast and endoderm. Definitive endoderm is characterized by the transient expression of primitive streak markers (LHX1, MIXL1, WNT3, LHX1, brachyury) and CXCR4, Sox17, HNF3b, Goosecoid and E-Cadherin. In contrast, primitive endoderm (visceral and parietal endoderm), which gives rise to the yolk sac, expresses Sox17, Sox7, and HNF3B. After gastrulation, embryonic progenitors of the digestive and respiratory organs initially exist in a single cell thick, epithelial sheet of endoderm that lines the ventral surface of the embryo. Then, the endoderm folds into a gut tube to form the foregut, midgut and hindgut endoderm. At ED8.25, ventral foregut is guided towards a hepatic fate under the influence of cytokines secreted by the adjacent cardiac mesoderm (aFGF-bFGF) and septum transversum mesenchyme (BMPs). After this specification (ED0.5-ED10), the resident cells of the primitive liver bud, consisting of bipotential hepatoblasts, undergo balanced events including proliferation, apoptosis, and differentiation to eventually constitute a functioning organ. This further maturation occurs through fibroblast growth factors (aFGF-FGF4-FGF8), Wnt signaling, factors secreted by the invading endothelial cells, the transiently (ED10) present hematopoietic cells in the fetal liver (Oncostatin M) and from the surrounding non-parenchymal cells (HGF). At ED14, bipotential hepatoblast become either fully mature hepatocytes or cholangiocytes. This determination depends upon the TGBβ/Activin and Notch2/Jagged1 signaling pathway.

SUMMARY OF THE INVENTION

The invention is based on methods developed by the inventors to produce a renewable source of hepatocytes in vitro. Cell culture conditions were developed in view of gene expression during embryonic liver development. The inventors developed specific cell culture conditions to successfully produce cells that express phenotypes of hepatocytes and endodermal progenitors. Numbered statements of the invention are as follows.

1. A method for inducing cells to differentiate into cells with a hepatocyte phenotype, comprising:
    (a) culturing cells with about 5 ng/ml to about 500 ng/ml Wnt3a and about 10 ng/ml to about 1,000 ng/ml ActivinA;
    (b) then culturing the cells of step (a) with about 1 ng/ml to about 100 ng/ml bFGF and about 5 ng/ml to about 500 ng/ml BMP4;
    (c) then culturing the cells of step (b) with about 5 ng/ml to about 500 ng/ml aFGF, about 1 ng/ml to about 100 ng/ml FGF4 and about 2.5 ng/ml to about 250 ng/ml FGF8b; and
    (d) then culturing the cells of step (c) with about 2 ng/ml to about 200 ng/ml HGF and about 10 ng/ml to about 1,000 ng/ml Follistatin.

2. The method of statement 1, wherein the cells are cultured in step (a) with about 50 ng/ml Wnt3a and about 100 ng/ml ActivinA.

3. The method of statement 1, wherein the cells are cultured in step (b) with about 10 ng/ml bFGF and about 50 ng/ml BMP4.

4. The method of statement 1, wherein the cells are cultured in step (c) with about 50 ng/ml aFGF, about 10 ng/ml FGF4 and about 25 ng/ml FGF8b.

5. The method of statement 1, wherein the cells are cultured in step (d) with about 20 ng/ml HGF and about 100 ng/ml Follistatin.

6. A method for inducing cells to differentiate into cells with a hepatocyte phenotype, comprising:
    (a) culturing the cells with about 50 ng/ml Wnt3a and about 100 ng/ml ActivinA;
    (b) then culturing the cells of step (a) with about 10 ng/ml bFGF and about 50 ng/ml BMP4;
    (c) then culturing the cells of step (b) with about 50 ng/ml aFGF, about 10 ng/ml FGF4 and about 25 ng/ml FGF8b; and
    (d) then culturing the cells of step (c) with about 20 ng/ml HGF and about 100 ng/ml Follistatin.

7. Cells produced according to any of the methods described herein.

8. A method for inducing cells that express a primitive endodermal phenotype into cells that express a definitive endodermal phenotype, comprising:
    (a) culturing cells that express a primitive endodermal phenotype with about 5 ng/ml to about 500 ng/ml Wnt3a and about 10 ng/ml to about 1,000 ng/ml ActivinA.

9. The method of statement 8, wherein the cells are cultured with about 50 ng/ml Wnt3a and about 100 ng/ml ActivinA.

10. A method for inducing cells that express a primitive endodermal phenotype into cells that express a definitive endodermal phenotype and then into cells that express a liver-committed endodermal phenotype, comprising:

(a) culturing cells that express a primitive endodermal phenotype with about 5 ng/ml to about 500 ng/ml Wnt3a and about 10 ng/ml to about 1,000 ng/ml ActivinA; and
(b) then culturing the cells of step (a) with about 1 ng/ml to about 100 ng/ml bFGF and about 5 ng/ml to about 500 ng/ml BMP4.

11. The method of statement 10, wherein the cells in step (a) are cultured with about 50 ng/ml Wnt3a and about 100 ng/ml ActivinA, and the cells in step (b) are cultured with about 10 ng/ml bFGF and about 50 ng/ml BMP4.

12. A method for inducing cells that express a primitive endodermal phenotype into cells that express a definitive endodermal phenotype, then into cells that express a liver-committed phenotype and then into cells that express a hepatoblast phenotype, comprising:
(a) culturing cells that express a primitive endodermal phenotype with about 5 ng/ml to about 500 ng/ml Wnt3a and about 10 ng/ml to about 1,000 ng/ml ActivinA;
(b) then culturing the cells of step (a) with about 1 ng/ml to about 100 ng/ml bFGF and about 5 ng/ml to about 500 ng/ml BMP4; and
(c) then culturing the cells of step (b) with about 5 ng/ml to about 500 ng/ml aFGF, about 1 ng/ml to about 100 ng/ml FGF4 and about 2.5 ng/ml to about 250 ng/ml FGF8b.

13. The method of statement 12, wherein the cells in step (a) are cultured with about 50 ng/ml Wnt3a and about 100 ng/ml ActivinA, the cells in step (b) are cultured with about 10 ng/ml bFGF and about 50 ng/ml BMP4, and the cells in step (c) are cultured with about 50 ng/ml aFGF, about 10 ng/ml FGF4 and about 25 ng/ml FGF8b.

14. A method for inducing cells that express a primitive endodermal phenotype into cells that express a definitive endodermal phenotype and then into cells that express a liver-committed phenotype and then into cells that express a hepatoblast phenotype and then into cells that express a hepatocyte phenotype, comprising:
(a) culturing cells that express a primitive endodermal phenotype with about 5 ng/ml to about 500 ng/ml Wnt3a and about 10 ng/ml to about 1,000 ng/ml ActivinA;
(b) then culturing the cells of step (a) with about 1 ng/ml to about 100 ng/ml bFGF and about 5 ng/ml to about 500 ng/ml BMP4;
(c) then culturing the cells of step (b) with about 5 ng/ml to about 500 ng/ml aFGF, about 1 ng/ml to about 100 ng/ml FGF4 and about 2.5 ng/ml to about 250 ng/ml FGF8b; and
(d) then culturing the cells of step (c) with about 2 ng/ml to about 200 ng/ml HGF and about 10 ng/ml to about 1,000 ng/ml Follistatin.

15. The method of statement 14, wherein the cells in step (a) are cultured with about 50 ng/ml Wnt3a and about 100 ng/ml ActivinA, the cells in step (b) are cultured with about 10 ng/ml bFGF and about 50 ng/ml BMP4, the cells in step (c) are cultured with about 50 ng/ml aFGF, about 10 ng/ml FGF4 and about 25 ng/ml FGF8b, and the cells of step (d) are cultured with about 20 ng/ml HGF and about 100 ng/ml Follistatin.

16. A method for inducing cells that express a definitive endodermal phenotype into cells that express a liver-committed phenotype, comprising
(a) culturing cells that express a definitive endodermal phenotype with about 1 ng/ml to about 100 ng/ml bFGF and about 5 ng/ml to about 500 ng/ml BMP4.

17. The method of statement 16, wherein the cells are cultured with about 10 ng/ml bFGF and about 50 ng/ml BMP4.

18. A method for inducing cells that express a definitive endodermal phenotype into cells that express a liver-committed endodermal phenotype and then into cells that express a hepatoblast phenotype, comprising:
(a) culturing cells that express a definitive endodermal phenotype with about 1 ng/ml to about 100 ng/ml bFGF and about 5 ng/ml to about 500 ng/ml BMP4; and
(b) then culturing the cells of step (a) with about 5 ng/ml to about 500 ng/ml aFGF, about 1 ng/ml to about 100 ng/ml FGF4 and about 2.5 ng/ml to about 250 ng/ml FGF8b.

19. The method of statement 18, wherein the cells in step (a) are cultured with about 10 ng/ml bFGF and about 50 ng/ml BMP4, and the cells in step (b) are cultured with about 50 ng/ml aFGF, about 10 ng/ml FGF4 and about 25 ng/ml FGF8b.

20. A method for inducing cells that express a definitive endodermal phenotype into cells that express a liver-committed phenotype and then into cells that express a hepatoblast phenotype and then into cells that express a hepatocyte phenotype, comprising:
(a) culturing cells that express a definitive endodermal phenotype with about 1 ng/ml to about 100 ng/ml bFGF and about 5 ng/ml to about 500 ng/ml BMP4;
(b) then culturing the cells of step (a) with about 5 ng/ml to about 500 ng/ml aFGF, about 1 ng/ml to about 100 ng/ml FGF4 and about 2.5 ng/ml to about 250 ng/ml FGF8b; and
(c) then culturing the cells of step (c) with about 2 ng/ml to about 200 ng/ml HGF and about 10 ng/ml to about 1,000 ng/ml Follistatin.

21. The method of statement 20, wherein the cells in step (a) are cultured with about 10 ng/ml bFGF and about 50 ng/ml BMP4, the cells in step (b) are cultured with about 50 ng/ml aFGF, about 10 ng/ml FGF4 and about 25 ng/ml FGF8b, and the cells in step (c) are cultured with about 20 ng/ml HGF and about 100 ng/ml Follistatin.

22. A method for inducing cells that express a liver-committed endodermal phenotype to differentiate into cells that express a hepatoblast phenotype, comprising:
(a) culturing cells that express a liver-committed endodermal phenotype with about 5 ng/ml to about 500 ng/ml aFGF, about 1 ng/ml to about 100 ng/ml FGF4 and about 2.5 ng/ml to about 250 ng/ml FGF8b.

23. The method of statement 22, wherein the cells are cultured with about 50 ng/ml aFGF, about 10 ng/ml FGF4 and about 25 ng/ml FGF8b.

24. A method for inducing cells that express a liver-committed phenotype into cells that express a hepatoblast phenotype and then into cells that express a hepatocyte phenotype, comprising:
(a) culturing cells that express a liver-committed phenotype with about 5 ng/ml to about 500 ng/ml aFGF, about 1 ng/ml to about 100 ng/ml FGF4 and about 2.5 ng/ml to about 250 ng/ml FGF8b; and
(b) then culturing the cells of step (a) with about 2 ng/ml to about 200 ng/ml HGF and about 10 ng/ml to about 1,000 ng/ml Follistatin.

25. The method of statement 24, wherein the cells in step (a) are cultured with about 50 ng/ml aFGF, about 10 ng/ml FGF4 and about 25 ng/ml FGF8b, and the cells in step (b) are cultured with about 20 ng/ml HGF and about 100 ng/ml Follistatin.

26. A method for inducing cells that express a hepatoblast phenotype into cells that express a hepatocyte phenotype, comprising:

(a) culturing cells that express a hepatoblast phenotype with about 2 ng/ml to about 200 ng/ml HGF and about 10 ng/ml to about 1,000 ng/ml Follistatin.

27. The method of statement 26, wherein the cells are cultured with about 20 ng/ml HGF and about 100 ng/ml Follistatin.

28. The methods herein, wherein the cells are cultured at one or more steps in a medium containing a serum concentration ranging from 0% to about 2%.

29. The method of statement 28, wherein the cells are cultured at one or more steps in a medium containing a serum concentration of about 2%.

30. The methods herein, wherein the cells are cultured at one or more steps in a medium containing about $10^{-4}$ M to about $10^{-7}$ M dexamethasone.

31. The method of statement 30, wherein the cells are cultured at one or more steps in a medium containing about $10^{-6}$ M dexamethasone.

32. The methods herein, wherein the cells are cultured at one or more steps for at least four days.

33. The method of statements herein, wherein the cells that express a primitive endodermal phenotype are cultured for about six days, the cells that express a definitive endodermal phenotype are cultured for about four days, the cells that express a liver-committed endodermal phenotype are cultured for about four days, and the cells that express a hepatoblast phenotype are cultured for about seven days.

34. The methods herein, wherein the cells are mammalian.

35. The method of statement 34, wherein the cells are human, mouse, or rat.

36. The methods herein, wherein the cells that are contacted with Wnt3A and Activin A are embryonic stem cells or cells that are not embryonic stem cells, embryonic germ cells or germ cells, and can differentiate into at least one cell type of each of the endodermal, ectodermal and mesodermal embryonic lineages.

37. The method of statement 36, wherein the cells are not embryonic germ cells, embryonic stem cells or germ cells, and can differentiate into at least one cell type of each of the endodermal, ectodermal and mesodermal embryonic lineages.

38. The method of statement 36, wherein the cells are embryonic stem cells.

39. The method of statement 37, wherein the cells are IPS cells.

40. The method of statement 37, wherein the cells are isolated from bone marrow, placenta, umbilical cord, muscle, brain, liver spinal cord, blood or skin. But they can be derived from any tissue or cell, and also by de-differentiation.

41. Cells produced according to any one of the methods recited in the preceding statements.

42. A composition, comprising cells that express a primitive endodermal phenotype in a culture medium comprising about 5 ng/ml to about 500 ng/ml Wnt3a and about 10 ng/ml to about 1,000 ng/ml ActivinA.

43. The composition of statement 42, wherein the medium is comprised of about 50 ng/ml Wnt3a and about 100 ng/ml ActivinA.

44. A composition, comprising cells that express a definitive endodermal phenotype in a culture medium comprising about 1 ng/ml to about 100 ng/ml bFGF and about 5 ng/ml to about 500 ng/ml BMP4.

45. The composition of statement 44, wherein the medium is comprised of about 10 ng/ml bFGF and about 50 ng/ml BMP4.

46. A composition, comprising cells that express a liver-committed endodermal phenotype in a culture medium comprising about 5 ng/ml to about 500 ng/ml aFGF, about 1 ng/ml to about 100 ng/ml FGF4 and about 2.5 ng/ml to about 250 ng/ml FGF8b.

47. The composition of statement 46, wherein the medium is comprised of about 50 ng/ml aFGF, about 10 ng/ml FGF4 and about 25 ng/ml FGF8b.

48. A composition, comprising cells that express a hepatoblast phenotype in a culture medium comprising about 2 ng/ml to about 200 ng/ml HGF and about 10 ng/ml to about 1,000 ng/ml Follistatin.

49. The composition of statement 48, wherein the medium is comprised of about 20 ng/ml HOF and about 100 ng/ml Follistatin.

50. The compositions herein, wherein the medium further comprises serum in a concentration from 0% to about 2%.

51. The composition of statement 50, wherein the serum concentration is about 2%.

52. The compositions herein, wherein the medium further comprises about $10^{-4}$ M to about $10^{-7}$ M dexamethasone.

53. The composition of statement 52, wherein the concentration of dexamethasone is about $10^{-6}$ M.

54. The compositions herein, wherein the cells are mammalian.

55. The composition of statement 54, wherein the cells are human.

56. The compositions herein, wherein the cells are embryonic stem cells or cells that are not embryonic stem cells, embryonic germ cells or germ cells, and can differentiate into at least one cell type of each of the endodermal, ectodermal and mesodermal embryonic lineages.

57. The composition of statement 56, wherein the cells are not embryonic germ cells, embryonic stem cells or germ cells, and can differentiate into at least one cell type of each of the endodermal, ectodermal and mesodermal embryonic lineages.

58. The composition of statement 56, wherein the cells are embryonic stem cells.

59. The composition of statement 57, wherein the cells are IPS cells.

60. The composition of statement 57, wherein the cells are isolated from bone marrow, placenta, umbilical cord, muscle, brain, liver spinal cord, blood or skin.

In one embodiment, the serum is fetal bovine serum.

In one embodiment, culturing cells with Wnt3a is about 2.5 days with a range of about 1.5-3.5 days, such as 2 or 3 days.

Any cell can be used in the initial step of culture with Wnt3a and Activin A as long as it has a phenotype of a cell that is prior to the primitive streak. Such a cell could express Oct3/4. For an embryonic stem cell, for example, the phenotype would be inner cell mass cell or epiblast. Cells include, but are not limited to, primordial germ cells, embryonic germ cells, cells produced by somatic cell nuclear transplantation into oocytes, tumor cell lines, embryonal carcinoma cells, blastomere cells, inner cell mass cells, embryonic stem cell cultures and lines, spermatogonial stem cells, epliblast cells, and other non-embryonic stem cells, such as reprogrammed somatic cells (IPSC). In one embodiment, such cells express Oct3/4 at levels greater than about 0.1% of Oct3/4 expression in embryonic stem cells.

Cells at any step (after the initial step with Wnt3a and Activin A) can be produced by the methods of the invention or can be derived from an in vivo or in vitro source. For example, definitive endodermal cells can be derived from in vivo and cultured according to the conditions described herein to produce cells with a liver-committed phenotype, cells with a liver-committed phenotype can be derived from in vivo and cultured according to the conditions described herein to produce cells with a hepatoblast phenotype, etc.

61. A pharmaceutical composition comprising the cells produced according to any one of the methods herein.

62. A method of treatment comprising administering a therapeutically effective amount of the cells produced according to any one of the methods herein to a subject with a liver deficiency.

The invention is also directed to methods of using the cells produced by the methods for treatment of liver deficiencies.

The invention is also directed to methods of using the cells for studies of liver metabolism, for example, to identify or assess metabolic modulators.

The invention is also directed to methods of using the cells for studies of liver toxicity, for example, to identify or assess the toxicity of specific compounds.

The invention is also directed to pharmaceutical compositions containing the cells of the invention. Such compositions are suitable for administration to subjects in need of such cells. The cells would be administered in therapeutically effective amounts.

DETAILED DESCRIPTION OF THE INVENTION

Definitions

Figure 1:
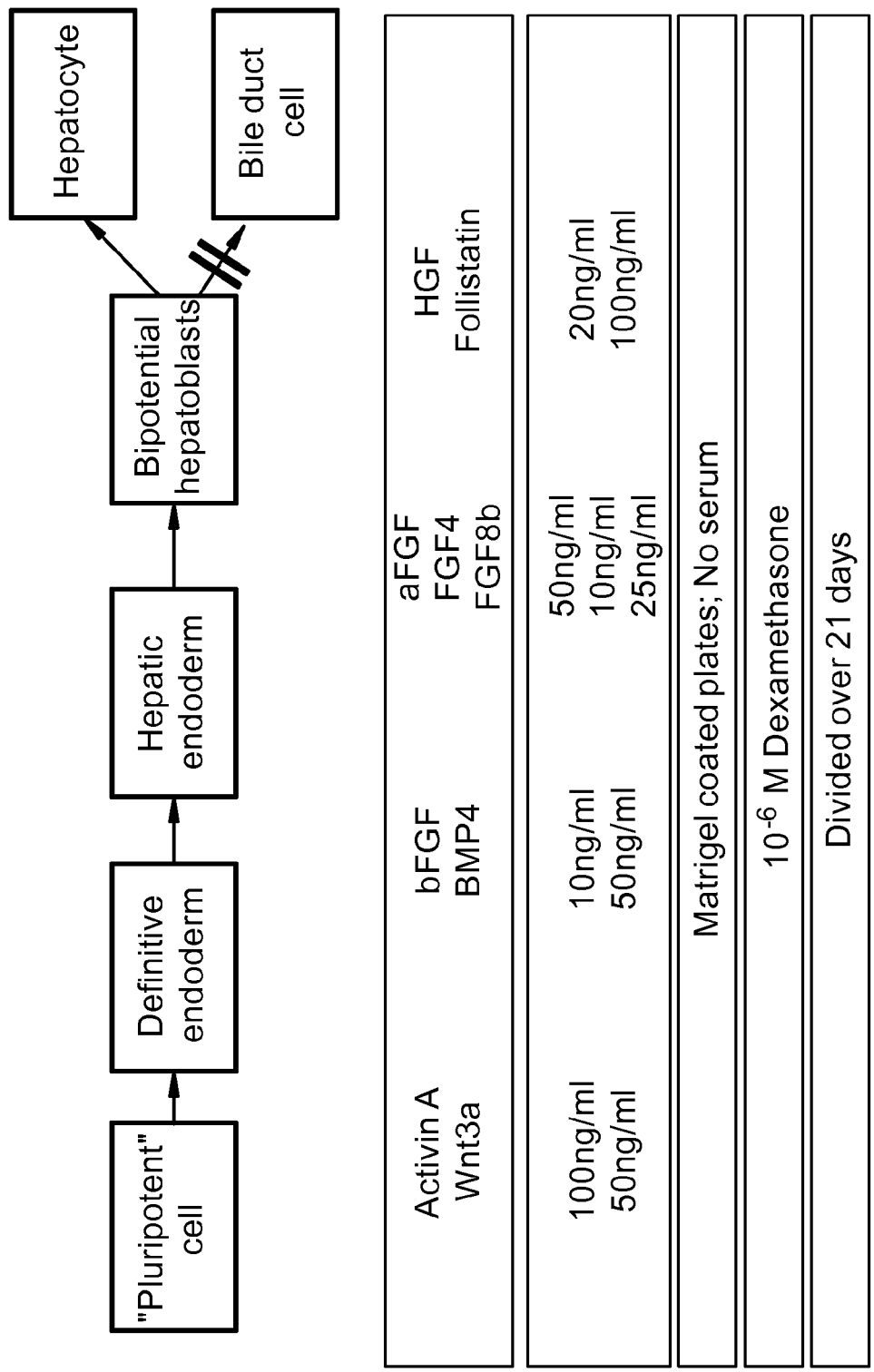
FIG. 1 provides the 4-step in vitro differentiation protocol. Days 0-6: Activin A (100 ng/ml) and Wnt3a (50 ng/ml). Days 6-10: bFGF (10 ng/ml) and BMP4 (50 ng/ml). Days 10-14: aFGF (50 ng/ml), FGF4 (10 ng/ml) and FGF8b (25 ng/ml). Days 14-21: HGF (20 ng/ml) and Follistatin (100 ng/ml).

"A" or "an" means one or more than one.

"Comprising" means, without other limitation, including the referent, necessarily, without any qualification or exclusion on what else may be included. For example, "a composition comprising x and y" encompasses any composition that contains x and y, no matter what other components may be present in the composition. Likewise, "a method comprising the step of x" encompasses any method in which x is carried out, whether x is the only step in the method or it is only one of the steps, no matter how many other steps there may be and no matter how simple or complex x is in comparison to them. "Comprised of" and similar phrases using words of the root "comprise" are used herein as synonyms of "comprising" and have the same meaning.

"Definitive endodermal phenotype" is a particular phenotype of cells that no longer express the self-renewal gene Oct3/4, do not express the primitive endoderm gene Sox7, do not express the mesodermal gene Flk1, but express Sox17, Foxa2, E-cadherin, CXCR4, and PDGF-Ra.

"Effective amount" generally means an amount which provides the desired local or systemic effect. For example, an effective amount is an amount sufficient to effectuate a beneficial or desired clinical result. The effective amounts can be provided all at once in a single administration or in fractional amounts that provide the effective amount in several administrations. The precise determination of what would be considered an effective amount may be based on factors individual to each subject, including their size, age, injury, and/or disease or injury being treated, and amount of time since the injury occurred or the disease began. One skilled in the art will be able to determine the effective amount for a given subject based on these considerations which are routine in the art. As used herein, "effective dose" means the same as "effective amount."

"EC cells" were discovered from analysis of a type of cancer called a teratocarcinoma. In 1964, researchers noted that a single cell in teratocarcinomas could be isolated and remain undifferentiated in culture. This type of stem cell became known as an embryonic carcinoma cell (EC cell).

"Embryonic Stem Cells (ESC)" are well known in the art and have been prepared from many different mammalian species for many years. Embryonic stem cells are stem cells derived from the inner cell mass of an early stage embryo known as a blastocyst. They are able to differentiate into all derivatives of the three primary germ layers: ectoderm, endoderm, and mesoderm. These include each of the more than 220 cell types in the adult body. The ES cells can become any tissue in the body, excluding placenta. Only the morula's cells are totipotent, able to become all tissues and a placenta.

"Hepatic differentiation factors" are chemical or biological factors that induce differentiation of stem and progenitor cells into more differentiated cells of the hepatic lineage. Hepatic differentiation factors include, but are not limited to, Wnt3a, ActivinA, bFGF, BMP4, aFGF, FGF4, FGF8b, HGF and Follistatin. The initial cell may express Oct3/4.

"Hepatoblast phenotype" is a particular phenotype of cells that co-express albumin, alpha fetoprotein and keratin 19, and express, on the cell membrane, c-Met, EPCAM, and Dlk1 (Tanimizu, N. et al., *J Cell Sci*, 116:1775-1786 (2003)).

"Hepatocyte phenotype" is a particular phenotype of cells that express albumin and keratin 18 but not alpha fetoprotein and keratin 19; in addition, hepatocytes may express one or more of TAT, MRP2, G6P, GLYS2, PEPCK, A1AT, BSEP, CX-32, NTCP, CYP7A1 (rat) and CYP3A4 (human).

Use of the term "includes" is not intended to be limiting. For example, stating that an inhibitor "includes fragments and variants does not mean that other forms of the inhibitor are excluded.

"Induced pluripotent stem cells (IPSC or IPS cells)" are somatic cells that have been reprogrammed for example, by introducing exogenous genes that confer on the somatic cell a less differentiated phenotype. These cells can then be induced to differentiate into less differentiated progeny. IPS cells have been derived using modifications of an approach originally discovered in 2006 (Yamanaka, S. et al., *Cell Stem Cell*, 1:39-49 (2007)). For example, in one instance, to create IPS cells, scientists started with skin cells that were then modified by a standard laboratory technique using retroviruses to insert genes into the cellular DNA. In one instance, the inserted genes were Oct4, Sox2, Lif4, and c-myc, known to act together as natural regulators to keep cells in an embryonic stem cell-like state. These cells have been described in the literature. See, for example, Wernig et al., *PNAS*, 105:5856-5861(2008); Jaenisch et al., *Cell*, 132:567-582 (2008); Hanna et al., *Cell*, 133:250-264 (2008); and Brambrink et al., *Cell Stem Cell*, 2:151-159 (2008). These references are incorporated by reference for teaching IPSCs and methods for producing them. It is also possible that such cells can be created by specific culture conditions (exposure to specific agents).

The term "isolated" refers to a cell or cells that are not associated with one or more cells or one or more cellular components that are associated with the cell or cells in vivo. An "enriched population" means a relative increase in numbers of a desired cell relative to one or more other cell types in vivo or in primary culture.

However, as used herein, the term "isolated" does not indicate the presence of only a specific desired cell, such as a stem or hepatic progenitor cell. Rather, the term "isolated" indicates that the cells are removed from their natural tissue environment and are present at a higher concentration as compared to the normal tissue environment. Accordingly, an "isolated" cell population may further include cell types in addition to stem cells and may include additional tissue components. This also can be expressed in terms of cell doublings, for examples. A cell may have undergone 10, 20, 30, 40 or more doublings in vitro or ex vivo so that it is enriched compared to its original numbers in vivo or in its original tissue environment (e.g., bone marrow, peripheral blood, adipose tissue, etc.)

"Liver-committed endodermal phenotype" is a particular phenotype of cells that are EPCAM positive and Dlk1 Negative (Tanimizu, N. et al., *J Cell Sci*, 116:1775-1786 (2003)).

"MAPC" is an acronym for "multipotent adult progenitor cell." It refers to a non-embryonic stem cell that can give rise to cell lineages of all three germ layers (i.e., endoderm, mesoderm and ectoderm) upon differentiation. Like embryonic stem cells, human MAPCs express telomerase, Oct 3/4 (i.e., Oct 3A), rex-1, rox-1 and sox-2, and may express SSEA-4. The term "adult" in MAPC is non-restrictive. It refers to a non-embryonic somatic cell.

MAPCs constitutively express Oct 3/4 and high levels of telomerase (Jiang, Y. et al., *Nature*, 418:41(2002); *Exp Hematol*, 30:896, 2002). MAPCs derived from human, mouse, rat or other mammals appear to be the only normal, non-malignant, somatic cell (i.e., non-germ cell) known to date to express very high levels of telomerase even in late passage cells. The telomeres are extended in MAPCs and they are karyotypically normal. Because MAPCs injected into a mammal can migrate to and assimilate within multiple organs, MAPCs are self-renewing stem cells.

"Multipotent," with respect to the term in "MAPC," refers to the ability to give rise to cell lineages of more than one primitive germ layer (i.e., endoderm, mesoderm and ectoderm) upon differentiation, such as all three. This term is not used consistently in the literature.

"Pluripotent" as used herein means any cell that, when exposed to Wnt3a and Activin A at the specified amounts, gives rise to cells with a definitive endodermal phenotype. Such cells may have the ability to give rise to cell lineages of more than one primitive germ layer (i.e., endoderm, mesoderm and ectoderm) upon differentiation, such as all three.

"Primitive endodermal phenotype" is a particular phenotype of cells that may express sox7, sox17, gata4, gata6, Cited1, Tcf2, Lamb1, Dab2, LamAl, LamA4, Lamc1, Col4a1, and Nidogen2 (this is a phenotype of mouse and rat MAPC, XEN cells from J. Rossant and Sox7 expressing ESC from J. Rossant. See also Ulloa-Montoya et al., *Genome Biol*, 8:R163 (2007); Se'guin et al., *Cell Stem Cell*, 3:182-195 (2008); and Kunath et al., *Development*, 132:1649-1661 (2005)).

"Primordial embryonic germ cells" (PG or EG cells) can be cultured and stimulated to produce many less differentiated cell types.

"Progenitor cells" are cells produced during differentiation of a stem cell that have some, but not all, of the characteristics of their terminally-differentiated progeny. The term "progenitor" as used in the acronym "MAPC" does not limit these cells to a particular lineage. A hepatocyte progenitor is any cell in the hepatocyte lineage that is less differentiated than a hepatocyte.

"Self-renewal" refers to the ability to produce replicate daughter stem cells having differentiation potential that is identical to those from which they arose. A similar term used in this context is "proliferation."

"Stem cell" means a cell that can undergo self-renewal (i.e., progeny with the same differentiation potential) and also produce progeny cells that are more restricted in differentiation potential. Within the context of the invention, a stem cell would also encompass a more differentiated cell that has dedifferentiated, for example, by nuclear transfer, by fusions with a more primitive stem cell, by introduction of specific transcription factors, or by culture under specific conditions. See, for example, Wilmut et al., *Nature*, 385:810-813 (1997); Ying et al., *Nature*, 416:545-548 (2002); Guan et al., *Nature*, 440:1199-1203 (2006); Takahashi et al., *Cell*, 126:663-676 (2006); Okita et al., *Nature*, 448:313-317 (2007); and Takahashi et al., *Cell*, 131:861-872 (2007).

Dedifferentiation may also be caused by the administration of certain compounds or exposure to a physical environment in vitro or in vivo that would cause the dedifferentiation. Stem cells also may be derived from abnormal tissue, such as a teratocarcinoma and some other sources such as embryoid bodies (although these can be considered embryonic stem cells in that they are derived from embryonic tissue, although not directly from the inner cell mass).

"Subject" means a vertebrate, such as a mammal, such as a human. Mammals include, but are not limited to, humans, dogs, cats, horses, cows and pigs.

The term "therapeutically effective amount" refers to the amount determined to produce any therapeutic response in a mammal. For example, effective amounts of the therapeutic cells or cell-associated agents may prolong the survivability of the patient, and/or inhibit overt clinical symptoms. Treatments that are therapeutically effective within the meaning of the term as used herein, include treatments that improve a subject's quality of life even if they do not improve the disease outcome per se. Such therapeutically effective amounts are ascertained by one of ordinary skill in the art through routine application to subject populations such as in clinical and pre-clinical trials. Thus, to "treat" means to deliver such an amount.

"Treat," "treating" or "treatment" are used broadly in relation to the invention and each such term encompasses, among others, preventing, ameliorating, inhibiting, or curing a deficiency, dysfunction, disease, or other deleterious process, including those that interfere with and/or result from a therapy.

Methods and Compositions of the Invention

The methods of the invention induce cells in culture to progress through the appropriate stages of hepatic development, thus recapitulating hepatic development in vitro and, as a result, give rise to cells having functional hepatic properties (e.g., biochemical and anatomical characteristics of hepatic cells).

Culture methods of the invention comprise a sequential addition of hepatic differentiation factors to cells, wherein there is a first addition of about 5 ng/ml to about 500 ng/ml Wnt3a, more particularly about 50 ng/ml Wnt3a, and about 10 ng/ml to about 1,000 ng/ml ActivinA, more particularly about 100 ng/ml ActivinA; a second addition of about 1 ng/ml to about 100 ng/ml bFGF, more particularly about 10 ng/ml bFGF, and 5 ng/ml to about 500 ng/ml BMP4, more particularly about 50 ng/ml BMP4; a third addition of 5 ng/ml to about 500 ng/ml aFGF, more particularly about 50 ng/ml aFGF, about 1 ng/ml to about 100 ng/ml FGF4, more particularly about 10 ng/ml FGF4, and about 2.5 ng/ml to about 250 ng/ml FGF8b, more particularly about 25 ng/ml FGF8b; and a fourth addition of about 2 ng/ml to about 200 ng/ml HGF, more particularly about 20 ng/ml HGF, and about 10 ng/ml to about 1,000 ng/ml Follistatin, more particularly about 100 ng/ml Follistatin.

At each successive step, the culture is continued for at least four days. More particularly, the cells are cultured in the first step for about six days; in the second step for about four days; in the third step for about four days; and in the fourth step for about seven days. In one embodiment, cells are cultured with Wnt3a for about 2.5 days.

At one or more steps, the cells are cultured in a medium containing a serum concentration from 0% to about 2%, more particularly about 2%.

Additionally, at one or more steps, the cells are cultured in a medium containing about $10^{-4}$ M to about $10^{-7}$ M dexamethasone, more particularly about $10^{-6}$ M dexamethasone.

Culture medium at each successive step of the methods of the present invention is prepared to contain only the growth factor(s) described above, and cells are washed between each step to reduce the presence of previously added growth factor(s). Alternatively, reduced concentrations of the previously provided factor(s) in a previous step can remain in the culture medium of the next step.

The methods of the present invention contemplate the use of any Wnt3a, ActivinA, bFGF, BMP4, aFGF, FGF4, FGF8b, HGF and Follistatin known in the art and having conserved function, and from all species (e.g., orthologs from human, mouse, rat, monkey, pig and the like). The hepatic differentiation factors of the present invention are well known to those skilled in the art.

Suitable forms of Wnt3a, ActivinA, bFGF, BMP4, aFGF, FGF4, FGF8b, HGF and Follistatin include, but are not limited to, isolated polypeptides, which are optionally recombinant, including whole proteins, partial proteins (e.g., domains) and peptide fragments. Fragments of a polypeptide preferably are those fragments that retain the distinct functional capability of the particular factor, which in the present invention generally relates to the ability to influence hepatic differentiation (the specific function of each factor is well known in the art). Such polypeptides also include, but are not limited to, fusion proteins and chimeric proteins. Short polypeptides can be synthesized chemically using well-established methods of peptide synthesis.

Cytokines may be replaced by small molecules that activate the same signal pathway, such as GSK3b inhibitor for Wnt3a; kinase activating molecules for the FGFs.

The culture methods of the present invention comprise a sequential addition of hepatic differentiation factors to cells.

In the first step of the present invention, the hepatic differentiation factors Wnt3a and Activin A are added to the cells.

The concentration of Wnt3a that is added to the cells can range from about 5 ng/ml to about 500 ng/ml. However, the invention also encompasses sub-ranges of concentrations of Wnt3a. For example, from about 5-25 ng/ml, 25-50 ng/ml, 50-75 ng/ml, 75-100 ng/ml, 100-150 ng/ml, 150-300 ng/ml and 300-500 ng/ml. The preferred concentration of Wnt3a that is added to the cells is about 50 ng/ml. The duration of Wnt3a exposure used in the examples is six days. However, this may be changed to two, three, four, or five days.

The concentration of Activin A that is added to the cells can range from about 10 ng/ml to about 1000 ng/ml. However, the invention also encompasses sub-ranges of concentrations of Activin A. For example, from about 10-25 ng/ml, 25-50 ng/ml, 50-75 ng/ml, 75-100 ng/ml, 100-125 ng/ml, 125-150 ng/ml, 150-175 ng/ml, 175-200 ng/ml, 200-400 ng/ml, 400-600 ng/ml, 600-800 ng/ml and 800-1000 ng/ml. The preferred concentration of Activin A that is added to the cells is about 100 ng/ml. The duration of Activin A exposure used in the examples is six days. However, this may be changed to four, five, or seven days.

In the second step of the present invention, the hepatic differentiation factors bFGF and BMP4 are added to the cells.

The concentration of bFGF that is added to the cells can range from about 1 ng/ml to about 100 ng/ml. However, the invention also encompasses sub-ranges of concentrations of bFGF. For example, from about 1-2 ng/ml, 2-4 ng/ml, 4-6 ng/ml, 6-8 ng/ml, 8-10 ng/ml, 10-12 ng/ml, 12-14 ng/ml, 14-16 ng/ml, 16-18 ng/ml, 18-20 ng/ml, 20-40 ng/ml, 40-60 ng/ml, 60-80 ng/ml and 80-100 ng/ml. The preferred concentration of bFGF that is added to the cells is about 10 ng/ml. The duration of bFGF exposure used in the examples is five days. However, this may be changed to four, six, or seven days.

The concentration of BMP4 that is added to the cells can range from about 5 ng/ml to about 500 ng/ml. However, the invention also encompasses sub-ranges of concentrations of BMP4. For example, from about 5-10 ng/ml, 10-20 ng/ml, 20-30 ng/ml, 30-40 ng/ml, 40-50 ng/ml, 50-60 ng/ml, 60-70 ng/ml, 70-80 ng/ml, 80-90 ng/ml, 90-100 ng/ml, 100-200 ng/ml, 200-300 ng/ml, 300-400 ng/ml and 400-500 ng/ml. The preferred concentration of BMP4 that is added to the cells is about 50 ng/ml. The duration of BMP4 exposure used in the examples is five days. However, this may be changed to four, six, or seven days.

In the third step of the present invention, the hepatic differentiation factors aFGF, FGF4 and FGF8b are added to the cells.

The concentration of aFGF that is added to the cells can range from about 5 ng/ml to about 500 ng/ml. However, the invention also encompasses sub-ranges of concentrations of aFGF. For example, from about 5-10 ng/ml, 10-20 ng/ml, 20-30 ng/ml, 30-40 ng/ml, 40-50 ng/ml, 50-60 ng/ml, 60-70 ng/ml, 70-80 ng/ml, 80-90 ng/ml, 90-100 ng/ml, 100-200 ng/ml, 200-300 ng/ml, 300-400 ng/ml and 400-500 ng/ml. The preferred concentration of aFGF that is added to the cells is about 50 ng/ml. The duration of aFGF exposure used in the examples is five days. However, this may be changed to four, six, or seven days.

The concentration of FGF4 that is added to the cells can range from about 1 ng/ml to about 100 ng/ml. However, the invention also encompasses sub-ranges of concentrations of FGF4. For example, from about 1-2 ng/ml, 2-4 ng/ml, 4-6 ng/ml, 6-8 ng/ml, 8-10 ng/ml, 10-20 ng/ml, 20-30 ng/ml, 30-40 ng/ml, 40-60 ng/ml, 60-80 ng/ml and 80-100 ng/ml. The preferred concentration of FGF4 that is added to the cells is about 10 ng/ml. The duration of FGF4 exposure used in the examples is five days. However, this may be changed to four, six, or seven days.

The concentration of FGF8b that is added to the cells can range from about 2.5 ng/ml to about 250 ng/ml. However, the invention also encompasses sub-ranges of concentrations of FGF8b. For example, from about 2.5-5 ng/ml, 5-10 ng/ml, 10-15 ng/ml, 15-20 ng/ml, 20-25 ng/ml, 25-30 ng/ml, 35-40 mg/ml, 45-50 ng/ml, 50-100 ng/ml, 100-150 ng/ml, 150-200 ng/ml and 200-250 ng/ml. The preferred concentration of FGF8b that is added to the cells is about 25 ng/ml. The duration of FGF8b exposure used in the examples is five days. However, this may be changed to four, six, or seven days.

In the fourth step of the present invention, the hepatic differentiation factors HGF and Follistatin are added to the cells.

The concentration of HGF that is added to the cells can range from about 2 ng/ml to about 200 ng/ml. However, the invention also encompasses sub-ranges of concentrations of HGF. For example, from about 2-5 ng/ml, 5-10 ng/ml, 10-15 ng/ml, 15-20 ng/ml, 20-25 ng/ml, 25-30 ng/ml, 30-35 ng/ml, 35-40 ng/ml, 40-50 ng/ml, 50-100 ng/ml, 100-150 ng/ml and 150-200 ng/ml. The preferred concentration of HGF that is added to the cells is about 20 ng/ml. The duration of HGF exposure used in the examples is five days. However, this may be changed to four, six, or seven days and can be as high as 30 days.

The concentration of Follistatin that is added to the cells can range from about 10 ng/ml to about 1000 ng/ml. However, the invention also encompasses sub-ranges of concentrations of Follistatin. For example, from about 10-25 ng/ml, 25-50 ng/ml, 50-75 ng/ml, 75-100 ng/ml, 100-125 ng/ml, 125-150 ng/ml, 150-175 ng/ml, 150-175 ng/ml, 175-200 ng/ml, 200-400 ng/ml, 400-600 ng/ml, 600-800 ng/ml and 800-1000 ng/ml. The preferred concentration of Follistatin that is added to the cells is about 100 ng/ml. The duration of Follistatin exposure used in the examples is five days. However, this may be changed to four, six, or seven days and can be as high as 30 days.

Stem Cells

The present invention can be practiced, preferably, using stem cells of vertebrate species, such as humans, non-human primates, domestic animals, livestock, and other non-human mammals.

Embryonic

Stem cells have been identified in most tissues. The most well studied stem cell is the embryonic stem cell (ESC), as it has unlimited self-renewal and multipotent differentiation potential. These cells are derived from the inner cell mass of the blastocyst or can be derived from the primordial germ cells of a post-implantation embryo (embryonal germ cells or EG cells). ES and EG cells have been derived, first from mouse, and later, from many different animals, and more recently, from non-human primates and humans. When introduced into mouse blastocysts or blastocysts of other animals, ESCs can contribute to all tissues of the animal. ES and EG cells can be identified by positive staining with antibodies against SSEA1 (mouse) and SSEA4 (human). See, for example, U.S. Pat. Nos. 5,453,357; 5,656,479; 5,670,372; 5,843,780; 5,874,301; 5,914,268; 6,110,739 6,190,910; 6,200,806; 6,432,711; 6,436,701, 6,500,668; 6,703,279; 6,875,607; 7,029,913; 7,112,437; 7,145,057; 7,153,684; and 7,294,508, each of which is incorporated by reference herein for teaching ESCs and methods of making and expanding ESCs. Accordingly, ESCs and methods for isolating and expanding ESCs are well-known in the art.

A number of transcription factors and exogenous cytokines have been identified that influence the potency status of embryonic stem cells in vivo. The first transcription factor to be described that is involved in stem cell pluripotency is Oct4. Oct4 belongs to the POU (Pit-Oct-Unc) family of transcription factors and is a DNA binding protein that is able to activate the transcription of genes, containing an octameric sequence called "the octamer motif" within the promotor or enhancer region. Oct4 is expressed at the moment of the cleavage stage of the fertilized zygote until the egg cylinder is formed. The function of Oct3/4 is to repress differentiation inducing genes (i.e., FoxaD3, hCG) and to activate genes promoting pluripotency (FGF4, Utf1, Rex1). Sox2, a member of the high mobility group (HMG) box transcription factors, cooperates with Oct4 to activate transcription of genes expressed in the inner cell mass. It is essential that Oct3/4 expression in embryonic stem cells is maintained between certain levels. Overexpression or downregulation of >50% of Oct4 expression level will alter embryonic stem cell fate, with the formation of primitive endoderm/mesoderm or trophectoderm, respectively. In vivo, Oct4 deficient embryos develop to the blastocyst stage, but the inner cell mass cells are not pluripotent. Instead they differentiate along the extraembryonic trophoblast lineage. Sall4, a mammalian Spalt transcription factor, is an upstream regulator of Oct4, and is therefore important to maintain appropriate levels of Oct4 during early phases of embryology. When Sall4 levels fall below a certain threshold, trophectodermal cells will expand ectopically into the inner cell mass. Another transcription factor required for pluripotency is Nanog, named after a celtic tribe "Tir Nan Og": the land of the ever young. In vivo, Nanog is expressed from the stage of the compacted morula, is subsequently defined to the inner cell mass and is downregulated by the implantation stage. Downregulation of Nanog may be important to avoid an uncontrolled expansion of pluripotent cells and to allow multilineage differentiation during gastrulation. Nanog null embryos, isolated at day 5.5, consist of a disorganized blastocyst, mainly containing extraembryonic endoderm and no discernable epiblast.

Non-Embryonic

An example of a non-embryonic stem cell is adipose-derived adult stem cells (ADSCs) which have been isolated from fat, typically by liposuction followed by release of the ADSCs using collagenase. ADSCs are similar in many ways to MSCs derived from bone marrow, except that it is possible to isolate many more cells from fat. These cells have been reported to differentiate into bone, fat, muscle, cartilage and neurons. A method of isolation has been described in U.S. 2005/0153442.

Other non-embryonic cells reported to be capable of differentiating into cell types of more than one embryonic germ layer include, but are not limited to, cells from umbilical cord blood (see U.S. Publication No. 2002/0164794), placenta (see U.S. Publication No. 2003/0181269; umbilical cord matrix (Mitchell, K. E. et al., *Stem Cells,* 21:50-60, 2003), small embryonic-like stem cells (Kucia, M. et al., *J Physiol Pharmacol,* 57 Suppl 5:5-18, 2006), amniotic fluid stem cells (Atala, A., *J Tissue Regen Med,* 1:83-96, 2007), skin-derived precursors (Toma et al., *Nat Cell Biol,* 3:778-784, 2001), and bone marrow (see U.S. Publication Nos. 2003/0059414 and 2006/0147246), each of which is incorporated by reference herein for teaching these cells.

Other stem cells that are known in the art include gastrointestinal stem cells, epidermal stem cells, and hepatic stem cells, which also have been termed "oval cells" (Potten, C., et al., *Trans R Soc Lond B Biol Sci,* 353:821-830 (1998);, Watt, F., *Trans R Soc Lond B Biol Sci,* 353:831(1997); Alison et al., *Hepatology,* 29:678-683 (1998).

Strategies of Reprogramming Somatic Cells

Several different strategies such as nuclear transplantation, cellular fusion, and culture induced reprogramming have been employed to induce the conversion of differentiated cells into an embryonic state. Nuclear transfer involves the injection of a somatic nucleus into an enucleated oocyte, which, upon transfer into a surrogate mother, can give rise to a clone ("reproductive cloning"), or, upon explantation in culture, can give rise to genetically matched embryonic stem (ES) cells ("somatic cell nuclear transfer," SCNT). Cell fusion of somatic cells with ES cells results in the generation of hybrids that show all features of pluripotent ES cells. Explantation of somatic cells in culture selects for immortal cell lines that may be pluripotent or multipotent. At present, spermatogonial stem cells are the only source of pluripotent cells that can be derived from postnatal animals. Transduction of somatic cells with defined factors can initiate reprogramming to a pluripotent state. These experimental approaches have been extensively reviewed (Hochedlinger and Jaenisch, *Nature,* 441:1061-1067 (2006) and Yamanaka, S., *Cell Stem Cell,* 1:39-49 (2007)).

Nuclear Transfer

Nuclear transplantation (NT), also referred to as somatic cell nuclear transfer (SCNT), denotes the introduction of a nucleus from a donor somatic cell into an enucleated ogocyte to generate a cloned animal such as Dolly the sheep (Wilmut et al., *Nature,* 385:810-813 (1997). The generation of live animals by NT demonstrated that the epigenetic state of somatic cells, including that of terminally differentiated cells, while stable, is not irreversible fixed but can be reprogrammed to an embryonic state that is capable of directing development of a new organism. In addition to providing an exciting experimental approach for elucidating the basic epigenetic mechanisms involved in embryonic development and disease, nuclear cloning technology is of potential interest for patient-specific transplantation medicine.

Fusion of Somatic Cells and Embryonic Stem Cells

Epigenetic reprogramming of somatic nuclei to an undifferentiated state has been demonstrated in murine hybrids produced by fusion of embryonic cells with somatic cells. Hybrids between various somatic cells and embryonic carcinoma cells (Softer, D., *Nat Rev Genet,* 7:319-327 (2006), embryonic germ (EG), or ES cells (Zwaka and Thomson, *Development,* 132:227-233 (2005)) share many features with the parental embryonic cells, indicating that the pluripotent phenotype is dominant in such fusion products. As with mouse (Tada et al., *Curr Biol,* 11:1553-1558 (2001)), human ES cells have the potential to reprogram somatic nuclei after fusion (Cowan et al., *Science,* 309:1369-1373 (2005)); Yu et al., *Science,* 318:1917-1920 (2006)). Activation of silent pluripotency markers such as Oct4 or reactivation of the inactive somatic X chromosome provided molecular evidence for reprogramming of the somatic genome in the hybrid cells. It has been suggested that DNA replication is essential for the activation of pluripotency markers, which is first observed 2 days after fusion (Do and Scholer, *Stem Cells,* 22:941-949 (2004)), and that forced overexpression of Nanog in ES cells promotes pluripotency when fused with neural stem cells (Silva et al., *Nature,* 441:997-1001(2006)).

Culture-Induced Reprogramming

Pluripotent cells have been derived from embryonic sources such as blastomeres and the inner cell mass (ICM) of the blastocyst (ES cells), the epiblast (EpiSC cells), primordial germ cells (EG cells), and postnatal spermatogonial stem cells ("maGSCsm" "ES-like" cells). The following pluripotent cells, along with their donor cell/tissue is as follows: parthogenetic ES cells are derived from murine oocytes (Narasimha et al., *Curr Biol,* 7:881-884 (1997)); embryonic stem cells have been derived from blastomeres (Wakayama et al., *Stem Cells,* 25:986-993 (2007)); inner cell mass cells (source not applicable) (Eggan et al., *Nature,* 428:44-49 (2004)); embryonic germ and embryonal carcinoma cells have been derived from primordial germ cells (Matsui et al., *Cell,* 70:841-847 (1992)); GMCS, maSSC, and MASC have been derived from spermatogonial stem cells (Guan et al., *Nature,* 440:1199-1203 (2006); Kanatsu-Shinohara et al., *Cell,* 119:1001-1012 (2004); and Seandel et al., *Nature,* 449: 346-350 (2007)); EpiSC cells are derived from epiblasts (Brons et al., *Nature,* 448:191-195 (2007); Tesar et al., *Nature,* 448:196-199 (2007)); parthogenetic ES cells have been derived from human oocytes (Cibelli et al., *Science,* 295L819 (2002); Revazova et al., *Cloning Stem Cells,* 9:432-449 (2007)); human ES cells have been derived from human blastocysts (Thomson et al., *Science,* 282:1145-1147 (1998)); MAPC have been derived from bone marrow (Jiang et al., *Nature,* 418:41-49 (2002); Phinney and Prockop, *Stem Cells,* 25:2896-2902 (2007)); cord blood cells (derived from cord blood) (van de Ven et al., *Exp Hematol,* 35:1753-1765 (2007)); neurosphere derived cells derived from neural cell (Clarke et al., *Science,* 288:1660-1663 (2000)). Donor cells from the germ cell lineage such as PGCs or spermatogonial stem cells are known to be unipotent in vivo, but it has been shown that pluripotent ES-like cells (Kanatsu-Shinohara et al., *Cell,* 119:1001-1012 (2004) or maGSCs (Guan et al., *Nature,* 440:1199-1203 (2006), can be isolated after prolonged in vitro culture. While most of these pluripotent cell types were capable of in vitro differentiation and teratoma formation, only ES, EG, EC, and the spermatogonial stem cell-derived maGCSs or ES-like cells were pluripotent by more stringent criteria, as they were able to form postnatal chimeras and contribute to the germline. Recently, multipotent adult spermatogonial stem cells (MASCs) were derived from testicular spermatogonial stem cells of adult mice, and these cells had an expression profile different from that of ES cells (Seandel et al., *Nature,* 449:346-350 (2007)) but similar to EpiSC cells, which were derived from the epiblast of postimplantation mouse embryos (Brons et al., *Nature,* 448: 191-195 (2007); Tesar et al., *Nature,* 448:196-199 (2007)).

Reprogramming by Defined Transcription Factors

Takahashi and Yamanaka have reported reprogramming somatic cells back to an ES-like state (Takahashi and Yamanaka, *Cell,* 126:663-676 (2006)). They successfully reprogrammed mouse embryonic fibroblasts (MEFs) and adult fibroblasts to pluripotent ES-like cells after viral-mediated transduction of the four transcription factors Oct4, Sox2, c-myc, and Klf4 followed by selection for activation of the Oct4 target gene Fbx15 (FIG. 2A). Cells that had activated Fbx15 were coined iPS (induced pluripotent stem) cells and were shown to be pluripotent by their ability to form teratomas, although the were unable to generate live chimeras. This pluripotent state was dependent on the continuous viral expression of the transduced Oct4 and Sox2 genes, whereas the endogenous Oct4 and Nanog genes were either not expressed or were expressed at a lower level than in ES cells, and their respective promoters were found to be largely methylated. This is consistent with the conclusion that the Fbx15-iPS cells did not correspond to ES cells but may have represented an incomplete state of reprogramming. While genetic experiments had established that Oct4 and Sox2 are essential for pluripotency (Chambers and Smith, Oncogene, 23:7150-7160 (2004); Ivanona et al., Nature, 442:5330538 (2006); Masui et al., Nat Cell Biol, 9:625-635 (2007)), the role of the two oncogenes c-myc and Klf4 in reprogramming is less clear. Some of these oncogenes may, in fact, be dispensable for reprogramming, as both mouse and human iPS cells have been obtained in the absence of c-myc transduction, although with low efficiency (Nakagawa et al., Nat Biotechnol, 26:191-106 (2008); Werning et al., Nature, 448:318-324 (2008); Yu et al., Science, 318: 1917-1920 (2007)).

MAPC

MAPC is an acronym for "multipotent adult progenitor cell" (non-ES, non-EG, non-germ). Genes found in ES cells also have been found in MAPCs (e.g., telomerase, Oct 3/4, rex-1, rox-1, sox-2). Oct 3/4 (Oct 3A in humans) appears to be specific for ES and germ cells. MAPC represents a more primitive progenitor cell population than MSC and demonstrates differentiation capability encompassing the epithelial, endothelial, neural, myogenic, hematopoietic, osteogenic, hepatogenic, chondrogenic and adipogenic lineages (Verfailie, C. M., Trends Cell Biol, 12:502-8, 2002, Jahagirdar, B. N., et al., Exp Hematol, 29:543-56, 2001; Reyes, M. and C. M. Verfaillie, Ann N Y Acad Sci, 938:231-233, 2001; Jiang, Y. et al., Exp Hematol, 30896-904, 2002; and Jiang, Y. et al., Nature, 418:41-9, 2002).

Human MAPCs are described in U.S. Pat. No. 7,015,037 and U.S. application Ser. No. 10/467,963. MAPCs have been identified in other mammals. Murine MAPCs, for example, also are described in U.S. Pat. No. 7,015,037 and U.S. application Ser. No. 10/467,963. Rat MAPCs also are described in U.S. application Ser. No. 10/467,963.

Isolation and Growth of MAPCs

Methods of MAPC isolation are known in the art. See, for example, U.S. Pat. No. 7,015,037 and U.S. application Ser. No. 10/467,963, and the methods contained therein, along with the characterization (phenotype) of MAPCs, which are incorporated herein by reference.

MAPCs were initially isolated from bone marrow, but subsequently were established from other tissues, including brain and muscle (Jiang, Y. et al., Exp Hematol, 30896-904, 2002). Thus, MAPCs can be isolated from multiple sources, including bone marrow, placenta, umbilical cord and cord blood, muscle, brain, liver, spinal cord, blood and skin. For example, MAPCs can be derived from bone marrow aspirates, which can be obtained by standard means available to those of skill in the art (see, for example, Muschler, G. F., et al., 1997; Batinic, D., et al., 1990). It, therefore, now is possible for those skilled in the art to obtain bone marrow aspirates, brain or liver biopsies, and other organs, and to isolate the cells using positive or negative selection techniques available to those skilled in the art, relying upon the genes that are expressed (or not expressed) in these cells (e.g., by functional or morphological assays such as those disclosed in the above-referenced applications, which have been incorporated herein by reference).

MAPCs from Human Bone Marrow

MAPCs do not express the common leukocyte antigen CD45 or erythroblast specific glycophorin-A (Gly-A). As described in U.S. Pat. No. 7,015,037, which is incorporated by reference herein for the methods disclosed therein, a mixed population of cells was subjected to a Ficoll Hypaque separation. The cells then were subjected to negative selection using anti-CD45 and anti-Gly-A antibodies, depleting the population of CD45$^+$ and Gly-A$^+$ cells, and the remaining approximately 0.1% of marrow mononuclear cells then were recovered. Cells also could be plated in fibronectin-coated wells and cultured as described below for 2-4 weeks to deplete the cells of CD45$^+$ and Gly-A$^+$ cells. In cultures of adherent bone marrow cells, many adherent stromal cells undergo replicative senescence around cell doubling 30 and a more homogeneous population of cells continues to expand and maintains long telomeres.

Alternatively, positive selection could be used to isolate cells via a combination of cell-specific markers. Both positive and negative selection techniques are available to those of skill in the art, and numerous monoclonal and polyclonal antibodies suitable for negative selection purposes are also available in the art (see, for example, Leukocyte Typing V, Schlossman, et al., Eds., 1995, Oxford University Press) and are commercially available from a number of sources.

Techniques for mammalian cell separation from a mixture of cell populations also have been described by Schwartz, et al. in U.S. Pat. No. 5,759,793 (magnetic separation), Basch et al., 1983 (immunoaffinity chromatography), and Wysocki and Sato, 1978 (fluorescence-activated cell sorting).

Culturing MAPC

MAPCs isolated as described herein can be cultured using methods disclosed herein and in U.S. Pat. No. 7,015,037, which is incorporated by reference herein for these methods.

Additional Culture Methods

In additional experiments, the density at which MAPCs are cultured can vary from about 100 cells/cm$^2$ to about 150 cells/cm$^2$ to about 10,000 cells/cm$^2$, including about 200 cells/cm$^2$ to about 1500 cells/cm$^2$ to about 2000 cells/cm$^2$. The density can vary between species. Additionally, optimal density can vary depending on culture conditions and source of cells. It is within the skill of the ordinary artisan to determine the optimal density for a given set of culture conditions and cells.

Also, effective atmospheric oxygen concentrations of less than about 10%, including about 3-5%, can be used at any time during the isolation, growth and differentiation of MAPCs in culture.

In an embodiment specific for MAPCs, supplements are cellular factors or components that allow MAPCs to retain the ability to differentiate into all three lineages. This may be indicated by the expression of specific markers of the undifferentiated state. MAPCs, for example, constitutively express Oct 3/4 (Oct 3A) and maintain high levels of telomerase. Assays for monitoring gene expression are well known in the art (e.g., RT-PCR) and can be conducted using standard methodology.

Cell Culture

In general, cells useful for the invention can be maintained and expanded in culture medium that is available to and well-known in the art. Such media include, but are not limited to, Dulbecco's Modified Eagle's Medium® (DMEM), DMEM F12 Medium®, Eagle's Minimum Essential Medium®, F-12K Medium®, Iscove's Modified Dulbecco's Medium® and RPMI-1640 Medium®. Many media are also available as low-glucose formulations, with or without sodium pyruvate.

Also contemplated in the present invention is supplementation of cell culture medium with mammalian sera. Sera often contain cellular factors and components that are necessary for viability and expansion. Examples of sera include fetal bovine serum (FBS), bovine serum (BS), calf serum (CS), fetal calf serum (FCS), newborn calf serum (NCS), goat serum (GS), horse serum (HS), human serum, chicken serum, porcine serum, sheep serum, rabbit serum, serum replacements and bovine embryonic fluid. It is understood that sera can be heat-inactivated at 55-65° C. if deemed necessary to inactivate components of the complement cascade.

Additional supplements also can be used advantageously to supply the cells with the necessary trace elements for optimal growth and expansion. Such supplements include insulin, transferrin, sodium selenium and combinations thereof. These components can be included in a salt solution such as, but not limited to, Hanks' Balanced Salt Solution® (HBSS), Earle's Salt Solution®, antioxidant supplements, MCDB-201® supplements, phosphate buffered saline (PBS), ascorbic acid and ascorbic acid-2-phosphate, as well as additional amino acids. Many cell culture media already contain amino acids, however, some require supplementation prior to culturing cells. Such amino acids include, but are not limited to, L-alanine, L-arginine, L-aspartic acid, L-asparagine, L-cysteine, L-cystine, L-glutamic acid, L-glutamine, L-glycine, L-histidine, L-isoleucine, L-leucine, L-lysine, L-methionine, L-phenylalanine, L-proline, L-serine, L-threonine, L-tryptophan, L-tyrosine, and L-valine. It is well within the skill of one in the art to determine the proper concentrations of these supplements.

Hormones also can be advantageously used in the cell cultures of the present invention and include, but are not limited to, D-aldosterone, diethylstilbestrol (DES), dexamethasone, β-estradiol, hydrocortisone, insulin, prolactin, progesterone, somatostatin/human growth hormone (HGH), thyrotropin, thyroxine and L-thyronine.

Lipids and lipid carriers also can be used to supplement cell culture media, depending on the type of cell and the fate of the differentiated cell. Such lipids and carriers can include, but are not limited to, cyclodextrin (α, β, γ), cholesterol, linoleic acid conjugated to albumin, linoleic acid and oleic acid conjugated to albumin, unconjugated linoleic acid, linoleic-oleic-arachidonic acid conjugated to albumin and oleic acid unconjugated and conjugated to albumin, among others.

Also contemplated in the present invention is the use of feeder cell layers. Feeder cells are used to support the growth of fastidious cultured cells such as ES cells. Feeder cells are normal cells that have been inactivated by γ-irradiation. In culture, the feeder layer serves as a basal layer for other cells and supplies cellular factors without further growth or division of their own (Lim, J. W. and Bodnar, A., 2002). Examples of feeder layer cells are typically human diploid lung cells, mouse embryonic fibroblasts and Swiss mouse embryonic fibroblasts, but can be any post-mitotic cell that is capable of supplying cellular components and factors that are advantageous in allowing optimal growth, viability and expansion of stem cells. In many cases, feeder cell layers are not necessary to keep ES cells in an undifferentiated, proliferative state, as leukemia inhibitory factor (LIF) has anti-differentiation properties. Therefore, supplementation with LIF can be used to maintain MAPC in some species in an undifferentiated state.

Cells may be cultured in low-serum or serum-free culture medium. Serum-free medium used to culture MAPCs is described in U.S. Pat. No. 7,015,037. Many cells have been grown in serum-free or low-serum medium. In this case, the medium is supplemented with one or more growth factors. Commonly used growth factors include, but are not limited to, bone morphogenic protein, basis fibroblast growth factor, platelet-derived growth factor and epidermal growth factor. See, for example, U.S. Pat. Nos. 7,169,610; 7,109,032; 7,037,721; 6,617,161; 6,617,159; 6,372,210; 6,224,860; 6,037,174; 5,908,782; 5,766,951; 5,397,706; and 4,657,866; all incorporated by reference herein for teaching growing cells in serum-free medium.

Cells in culture can be maintained either in suspension or attached to a solid support, such as extracellular matrix components. Stem cells often require additional factors that encourage their attachment to a solid support, such as type I and type II collagen, chondroitin sulfate, fibronectin, "super-fibronectin" and fibronectin-like polymers, gelatin, poly-D and poly-L-lysine, thrombospondin and vitronectin. One embodiment of the present invention utilizes fibronectin. See, for example, Ohashi et al., *Nature Medicine*, 13:880-885 (2007); Matsumoto et al., *J Bioscience and Bioengineering*, 105:350-354 (2008); Kirouac et al., *Cell Stem Cell*, 3:369-381(2008); Chua et al., *Biomaterials*, 26:2537-2547 (2005); Drobinskaya et al., *Stem Cells*, 26:2245-2256 (2008); Dvir-Ginzberg et al., FASEB J, 22:1440-1449 (2008); Turner et al., *J Biomed Mater Res Part B: Appl Biomater,* 82B:156-168 (2007); and Miyazawa et al., *Journal of Gastroenterology and Hepatology,* 22:1959-1964 (2007)).

Cells may also be grown in "3D" (aggregated) cultures. An example is U.S. Provisional Patent Application No. 61/022,121, filed Jan. 18, 2008.

Once established in culture, cells can be used fresh or frozen and stored as frozen stocks, using, for example, DMEM with 40% FCS and 10% DMSO. Other methods for preparing frozen stocks for cultured cells also are available to those skilled in the art.

Methods of identifying and subsequently separating differentiated cells from their undifferentiated counterparts can be carried out by methods well known in the art. Cells that have been induced to differentiate using methods of the present invention can be identified by selectively culturing cells under conditions whereby differentiated cells outnumber undifferentiated cells. Similarly, differentiated cells can be identified by morphological changes and characteristics that are not present on their undifferentiated counterparts, such as cell size and the complexity of intracellular organelle distribution. Also contemplated are methods of identifying differentiated cells by their expression of specific cell-surface markers such as cellular receptors and transmembrane proteins. Monoclonal antibodies against these cell-surface markers can be used to identify differentiated cells. Detection of these cells can be achieved through fluorescence activated cell sorting (FACS) and enzyme-linked immunosorbent assay (ELISA). From the standpoint of transcriptional upregulation of specific genes, differentiated cells often display levels of gene expression that are different from undifferentiated cells. Reverse-transcription polymerase chain reaction, or RT-PCR, also can be used to monitor changes in gene expression in response to differentiation. Whole genome analysis using microarray technology also can be used to identify differentiated cells.

Accordingly, once differentiated cells are identified, they can be separated from their undifferentiated counterparts, if necessary. The methods of identification detailed above also provide methods of separation, such as FACS, preferential cell culture methods, ELISA, magnetic beads and combinations thereof. One embodiment of the present invention comtemplates the use of FACS to identify and separate cells based on cell-surface antigen expression.

Pharmaceutical Formulations

Any of the cells produced by the methods described herein can be used in the clinic to treat a subject. They can, therefore, be formulated into a pharmaceutical composition. Therefore, in certain embodiments, the isolated or purified cell populations are present within a composition adapted for and suitable for delivery, i.e., physiologically compatible. Accordingly, compositions of the cell populations will often further comprise one or more buffers (e.g., neutral buffered saline or phosphate buffered saline), carbohydrates (e.g., glucose, mannose, sucrose or dextrans), mannitol, proteins, polypeptides or amino acids such as glycine, antioxidants, bacteriostats, chelating agents such as EDTA or glutathione, adjuvants (e.g., aluminum hydroxide), solutes that render the formulation isotonic, hypotonic or weakly hypertonic with the blood of a recipient, suspending agents, thickening agents and/or preservatives.

In other embodiments, the isolated or purified cell populations are present within a composition adapted for or suitable for freezing or storage.

In many embodiments the purity of the cells for administration to a subject is about 100%. In other embodiments it is 95% to 100%. In some embodiments it is 85% to 95%. Particularly in the case of admixtures with other cells, the percentage can be about 10%-15%, 15%-20%, 20%-25%, 25%-30%, 30%-35%, 35%-40%, 40%-45%, 45%-50%, 60%-70%, 70%-80%, 80%-90%, or 90%-95%. Or isolation/purity can be expressed in terms of cell doublings where the cells have undergone, for example, 10-20, 20-30, 30-40, 40-50 or more cell doublings.

The numbers of cells in a given volume can be determined by well known and routine procedures and instrumentation. The percentage of the cells in a given volume of a mixture of cells can be determined by much the same procedures. Cells can be readily counted manually or by using an automatic cell counter. Specific cells can be determined in a given volume using specific staining and visual examination and by automated methods using specific binding reagent, typically antibodies, fluorescent tags, and a fluorescence activated cell sorter.

The choice of formulation for administering the cells for a given application will depend on a variety of factors. Prominent among these will be the species of subject, the nature of the disorder, dysfunction, or disease being treated and its state and distribution in the subject, the nature of other therapies and agents that are being administered, the optimum route for administration, survivability via the route, the dosing regimen, and other factors that will be apparent to those skilled in the art. In particular, for instance, the choice of suitable carriers and other additives will depend on the exact route of administration and the nature of the particular dosage form.

For example, cell survival can be an important determinant of the efficacy of cell-based therapies. This is true for both primary and adjunctive therapies. Another concern arises when target sites are inhospitable to cell seeding and cell growth. This may impede access to the site and/or engraftment there of therapeutic cells. Various embodiments of the invention comprise measures to increase cell survival and/or to overcome problems posed by barriers to seeding and/or growth.

Final formulations of the aqueous suspension of cells/medium will typically involve adjusting the ionic strength of the suspension to isotonicity (i.e., about 0.1 to 0.2) and to physiological pH (i.e., about pH 6.8 to 7.5). The final formulation will also typically contain a fluid lubricant, such as maltose, which must be tolerated by the body. Exemplary lubricant components include glycerol, glycogen, maltose and the like. Organic polymer base materials, such as polyethylene glycol and hyaluronic acid as well as non-fibrillar collagen, preferably succinylated collagen, can also act as lubricants. Such lubricants are generally used to improve the injectability, intrudability and dispersion of the injected biomaterial at the site of injection and to decrease the amount of spiking by modifying the viscosity of the compositions. This final formulation is by definition the cells in a pharmaceutically acceptable carrier.

The cells are subsequently placed in a syringe or other injection apparatus for precise placement at the site of the tissue defect. The term "injectable" means the formulation can be dispensed from syringes having a gauge as low as 25 under normal conditions under normal pressure without substantial spiking. Spiking can cause the composition to ooze from the syringe rather than be injected into the tissue. For this precise placement, needles as fine as 27 gauge (200 µI.D.) or even 30 gauge (150 µI.D.) are desirable. The maximum particle size that can be extruded through such needles will be a complex function of at least the following: particle maximum dimension, particle aspect ratio (length:width), particle rigidity, surface roughness of particles and related factors affecting particle:particle adhesion, the viscoelastic properties of the suspending fluid, and the rate of flow through the needle. Rigid spherical beads suspended in a Newtonian fluid represent the simplest case, while fibrous or branched particles in a visco elastic fluid are likely to be more complex.

The desired isotonicity of the compositions of this invention may be accomplished using sodium chloride, or other pharmaceutically acceptable agents such as dextrose, boric acid, sodium tartrate, propylene glycol, or other inorganic or organic solutes. Sodium chloride is preferred particularly for buffers containing sodium ions.

Viscosity of the compositions, if desired, can be maintained at the selected level using a pharmaceutically acceptable thickening agent. Methylcellulose is preferred because it is readily and economically available and is easy to work with. Other suitable thickening agents include, for example, xanthan gum, carboxymethyl cellulose, hydroxypropyl cellulose, carbomer, and the like. The preferred concentration of the thickener will depend upon the agent selected. The important point is to use an amount, which will achieve the selected viscosity. Viscous compositions are normally prepared from solutions by the addition of such thickening agents.

A pharmaceutically acceptable preservative or stabilizer can be employed to increase the life of cell/medium compositions. If such preservatives are included, it is well within the purview of the skilled artisan to select compositions that will not affect the viability or efficacy of the cells.

Those skilled in the art will recognize that the components of the compositions should be chemically inert. This will present no problem to those skilled in chemical and pharmaceutical principles. Problems can be readily avoided by reference to standard texts or by simple experiments (not involving undue experimentation) using information provided by the disclosure, the documents cited herein, and generally available in the art.

Sterile injectable solutions can be prepared by incorporating the cells/medium utilized in practicing the present invention in the required amount of the appropriate solvent with various amounts of the other ingredients, as desired.

In some embodiments, cells/medium are formulated in a unit dosage injectable form, such as a solution, suspension, or emulsion. Pharmaceutical formulations suitable for injection of cells/medium typically are sterile aqueous solutions and dispersions. Carriers for injectable formulations can be a solvent or dispersing medium containing, for example, water, saline, phosphate buffered saline, polyol (for example, glycerol, propylene glycol, liquid polyethylene glycol, and the like), and suitable mixtures thereof.

The skilled artisan can readily determine the amount of cells and optional additives, vehicles, and/or carrier in compositions to be administered in methods of the invention. Typically, any additives (in addition to the cells) are present in an amount of 0.001 to 50 wt % in solution, such as in phosphate buffered saline. The active ingredient is present in the order of micrograms to milligrams, such as about 0.0001 to about 5 wt %, preferably about 0.0001 to about 1 wt %, most preferably about 0.0001 to about 0.05 wt % or about 0.001 to about 20 wt %, preferably about 0.01 to about 10 wt %, and most preferably about 0.05 to about 5 wt %.

In some embodiments cells are encapsulated for administration, particularly where encapsulation enhances the effectiveness of the therapy, or provides advantages in handling and/or shelf life. Encapsulation in some embodiments where it increases the efficacy of cell mediated immunosuppression may, as a result, also reduce the need for immunosuppressive drug therapy.

Also, encapsulation in some embodiments provides a barrier to a subject's immune system that may further reduce a subject's immune response to the cells (which generally are not immunogenic or are only weakly immunogenic in allogeneic transplants), thereby reducing any graft rejection or inflammation that might occur upon administration of the cells.

Cells may be encapsulated by membranes, as well as capsules, prior to implantation. It is contemplated that any of the many methods of cell encapsulation available may be employed. In some embodiments, cells are individually encapsulated. In some embodiments, many cells are encapsulated within the same membrane. In embodiments in which the cells are to be removed following implantation, a relatively large size structure encapsulating many cells, such as within a single membrane, may provide a convenient means for retrieval.

A wide variety of materials may be used in various embodiments for microencapsulation of cells. Such materials include, for example, polymer capsules, alginate-poly-L-lysine-alginate microcapsules, barium poly-L-lysine alginate capsules, barium alginate capsules, polyacrylonitrile/polyvinylchloride (PAN/PVC) hollow fibers, and polyethersulfone (PES) hollow fibers.

Techniques for microencapsulation of cells that may be used for administration of cells are known to those of skill in the art and are described, for example, in Chang, P., et al., 1999; Matthew, H. W., et al., 1991; Yanagi, K., et al., 1989; Cai Z. H., et al., 1988; Chang, T. M., 1992 and in U.S. Pat. No. 5,639,275 (which, for example, describes a biocompatible capsule for long-term maintenance of cells that stably express biologically active molecules. Additional methods of encapsulation are in European Patent Publication No. 301,777 and U.S. Pat. Nos. 4,353,888; 4,744,933; 4,749,620; 4,814,274; 5,084,350; 5,089,272; 5,578,442; 5,639,275; and 5,676,943. All of the foregoing are incorporated herein by reference in parts pertinent to encapsulation of cells.

Certain embodiments incorporate cells into a polymer, such as a biopolymer or synthetic polymer. Examples of biopolymers include, but are not limited to, fibronectin, fibrin, fibrinogen, thrombin, collagen, and proteoglycans. Other factors, such as the cytokines discussed above, can also be incorporated into the polymer. In other embodiments of the invention, cells may be incorporated in the interstices of a three-dimensional gel. A large polymer or gel, typically, will be surgically implanted. A polymer or gel that can be formulated in small enough particles or fibers can be administered by other common, more convenient, non-surgical routes.

In the case of treating liver deficiency, in particular, the cells may be enclosed in a device that can be implanted in a subject. Cells can be implanted in or near the liver or elsewhere to replace or supplement liver function. Cells can also be implanted without being in a device, e.g., in existing liver tissue.

Dosing

Compositions can be administered in dosages and by techniques well known to those skilled in the medical and veterinary arts taking into consideration such factors as the age, sex, weight, and condition of the particular patient, and the formulation that will be administered (e.g., solid vs. liquid). Doses for humans or other mammals can be determined without undue experimentation by the skilled artisan, from this disclosure, the documents cited herein, and the knowledge in the art.

The dose of cells/medium appropriate to be used in accordance with various embodiments of the invention will depend on numerous factors. It may vary considerably for different circumstances. The parameters that will determine optimal doses to be administered for primary and adjunctive therapy generally will include some or all of the following: the disease being treated and its stage; the species of the subject, their health, gender, age, weight, and metabolic rate; the subject's immunocompetence; other therapies being administered; and expected potential complications from the subject's history or genotype. The parameters may also include: whether the cells are syngeneic, autologous, allogeneic, or xenogeneic; their potency (specific activity); the site and/or distribution that must be targeted for the cells/medium to be effective; and such characteristics of the site such as accessibility to cells/medium and/or engraftment of cells. Additional parameters include co-administration with other factors (such as growth factors and cytokines). The optimal dose in a given situation also will take into consideration the way in which the cells/medium are formulated, the way they are administered, and the degree to which the cells/medium will be localized at the target sites following administration. Finally, the determination of optimal dosing necessarily will provide an effective dose that is neither below the threshold of maximal beneficial effect nor above the threshold where the deleterious effects associated with the dose outweighs the advantages of the increased dose.

The optimal dose of cells for some embodiments will be in the range of doses used for autologous, mononuclear bone marrow transplantation. For fairly pure preparations of cells, optimal doses in various embodiments will range from $10^4$ to $10^8$ cells/kg of recipient mass per administration. In some embodiments the optimal dose per administration will be between $10^5$ to $10^7$ cells/kg. In many embodiments the optimal dose per administration will be $5 \times 10^5$ to $5 \times 10^6$ cells/kg. By way of reference, higher doses in the foregoing are analogous to the doses of nucleated cells used in autologous mononuclear bone marrow transplantation. Some of the lower doses are analogous to the number of $CD34^+$ cells/kg used in autologous mononuclear bone marrow transplantation.

It is to be appreciated that a single dose may be delivered all at once, fractionally, or continuously over a period of time. The entire dose also may be delivered to a single location or spread fractionally over several locations.

In various embodiments, cells/medium may be administered in an initial dose, and thereafter maintained by further administration. Cells/medium may be administered by one method initially, and thereafter administered by the same method or one or more different methods. The levels can be maintained by the ongoing administration of the cells/medium. Various embodiments administer the cells/medium either initially or to maintain their level in the subject or both by intravenous injection. In a variety of embodiments, other forms of administration, are used, dependent upon the patient's condition and other factors, discussed elsewhere herein.

It is noted that human subjects are treated generally longer than experimental animals; but, treatment generally has a length proportional to the length of the disease process and the effectiveness of the treatment. Those skilled in the art will take this into account in using the results of other procedures carried out in humans and/or in animals, such as rats, mice, non-human primates, and the like, to determine appropriate doses for humans. Such determinations, based on these considerations and taking into account guidance provided by the present disclosure and the prior art will enable the skilled artisan to do so without undue experimentation.

Suitable regimens for initial administration and further doses or for sequential administrations may all be the same or may be variable. Appropriate regimens can be ascertained by the skilled artisan, from this disclosure, the documents cited herein, and the knowledge in the art.

The dose, frequency, and duration of treatment will depend on many factors, including the nature of the disease, the subject, and other therapies that may be administered. Accordingly, a wide variety of regimens may be used to administer the cells/medium.

In some embodiments cells/medium are administered to a subject in one dose. In others cells/medium are administered to a subject in a series of two or more doses in succession. In some other embodiments wherein cells/medium are administered in a single dose, in two doses, and/or more than two doses, the doses may be the same or different, and they are administered with equal or with unequal intervals between them.

Cells/medium may be administered in many frequencies over a wide range of times. In some embodiments, they are administered over a period of less than one day. In other embodiment they are administered over two, three, four, five, or six days. In some embodiments they are administered one or more times per week, over a period of weeks. In other embodiments they are administered over a period of weeks for one to several months. In various embodiments they may be administered over a period of months. In others they may be administered over a period of one or more years. Generally lengths of treatment will be proportional to the length of the disease process, the effectiveness of the therapies being applied, and the condition and response of the subject being treated.

Uses for the Cells

The liver plays a major role in metabolism, including plasma protein synthesis (e.g. albumin and coagulation factors), glycogen storage, decomposition of red blood cells, and detoxification. One of the major impediments to the use of hepatocytes in at least four areas of medicine is, in general, the scarcity of human hepatocytes.

(1) Therapy of Liver Failure with Hepatocyte Transplantation:

One of the unique features of the liver is its enormous natural regeneration ability. This regeneration is due in large part to the re-entry of terminally differentiated hepatocytes in the cell cycle, resulting in multiple cell divisions to regenerate the liver. When the hepatocytes are damaged, liver stem/progenitor cells, termed oval cells in rodents, located in the peri-portal zone, are activated and differentiate to mature hepatocytes (ref). Hence, most liver diseases ending in liver failure are caused by a combination of decreased proliferation of hepatocytes and exhaustion of the stem/progenitor cell pool. Liver failure is caused by a number of disorders, including cirrhosis due to infections, excessive alcohol consumption, genetic and idiopathic reasons. In addition, acute liver failure is caused by ingestion of certain drugs or foods. Liver transplantation is the only successful treatment for end stage liver disease, and is in many instances also the only curative therapy for certain forms of genetic disorders of the liver. Many liver disorders treated by whole liver transplantation result from hepatocyte dysfunction. As a consequence, there has been great interest in hepatocyte transplantation for the treatment of acute and chronic liver failure, as well as inherited metabolic disorders. There is significant evidence that grafted hepatocytes can assume the full range of liver functions in vivo. Hepatocyte transplantation has several advantages over whole liver transplant: lower morbidity, a single donor organ can be used for several recipients, cells can be cryopreserved, and cells grafts are less immunogenic than whole organ grafts. However, lack of donor cells curtails further exploration of this therapy.

Accordingly the invention is also directed to methods of treating liver deficiencies by administering the cells of the invention to a subject with the liver deficiency. Such deficiencies include, but are not limited to, toxic liver disease, metabolic liver disease, acute liver necrosis, effects of acetaminophen, hemochromatosis, Wilson's Disease, Crigler Najar, hereditary tyrosinemia, familial intrahepatic cholestatis type 3, ornithine transcarbamylase (OTC) deficiency, and urea cycle disorder.

Further diseases include, but are not limited to viral hepatitis, chronic viral hepatitis A, B, C, acute hepatitis A, B, C, D, E, cytomegalovirus and herpes simplex virus; liver dysfunction in other infectious diseases such as, without limitation, toxoplasmosis, hepatosplenic schistosomiasis, liver disease in syphilis, leptospirosis and amoebiasis; metabolic diseases such as, without limitation, haemochromatosis, Gilbert's syndrome, Dubin-Johnson syndrome and Rotor's syndrome; alcoholic liver disease such as, without limitation, fatty liver, fibrosis, sclerosis and cirrhosis; and toxic liver disease.

(2) Bioartificial Liver (BAL) Devices

In patients with terminal liver failure, the use of bioartificial liver devices has been proposed to bridge the time to liver transplantation (ref). BAL devices are designed to support the detoxification functions performed by the liver, hence decreasing the risk and severity of CNS complications associated with acute liver failure. BAL devices could benefit three groups of patients; those with fulminant hepatic failure, those waiting for an imminent transplant, and those with early failure of a liver transplant. Although some positive results have been seen in patients with liver failure, further exploration of the usefulness of BAL devices has been hampered by lack of suitable cells. Currently, tumor-derived cell lines or animal cells, which might be associated with possible tumor cell seeding, immune responses, and xeno-zoonoses, are used. The availability of cells with full mature hepatic function of human origin, would enable investigators to further test and optimize BAL devices to bridge patients till the liver spontaneously regenerates or a donor-liver is available. Although clinical trials have in general not been successful, some encouraging results have been seen in patients with acute liver failure. Accordingly, the cells of the invention can be used in such bioartificial liver devices.

(3) Pharmaceutical Testing

Pharmaceutical testing is moving more and more from in vivo experimentation to in vitro studies. Over the past decade, in vitro models were established, such as precision-cut liver slices, primary hepatocytes, and liver cell lines. A few studies examining the relevance of drug testing with hepatocyte cell lines, found that cell lines poorly reproduce and predict drug metabolism and hepatotoxicity as opposed to primary hepatocytes or liver slices. Thus, primary human hepatocytes are the "gold standard" for in vitro drug testing. However, the limited supply of human hepatocytes and the fact that such hepatocytes may not represent the genetic variation in society, limit the possibility of detecting potential drug toxicities. Consequently, development of stem cells from a diverse group of donors (for instance by generating IPS cells) and differentiation to hepatocytes with differing cytochrome P450 profiles would allow drug testing to more closely examine and predict potential problems for particular groups or individuals.

Accordingly, the cells of the invention can be used in such testing methods.

(4) Study of and Drug Development Against Human Hepatitis Viruses

A final area where generating hepatocytes from stem cells would aid human health significantly is in the area of viral hepatitis. Most in vitro studies on the hepatitis viruses have involved primary human hepatocytes. However, again, the limited availability of human tissue and also subject to the variability of the source material impedes these types of studies.

Accordingly, the cells of the invention can be used in such studies and in drug development.

The present invention is additionally described by way of the following illustrative, non-limiting Example that provides a better understanding of the present invention and of its many advantages.

EXAMPLES

Example 1

I. Methodology

1. Rat MAPC Culture

A rat MAPC cell line was derived from bone marrow of a male Fischer (F344) rat by Prof. Y. Jiang at the University of Minnesota, Minneapolis, USA. This established rat MAPC line was used in the experiments described below. Undifferentiated rat MAPCs were cultured at low cell density (~300 cells/cm$^2$) in low serum (2%) and oxygen (5%) conditions. Expansion medium consisted of DMEM (60%), MCDB (40%) supplemented with leukemia inhibiting factor (LIF), growth factors (10 ng/ml PDGF and 10 ng/ml EGF), dexamethasone ($5\times10^{-8}$ M), penicillin and streptomycin ($1\times$), ascorbic acid ($1\times$), beta-mercaptoethanol and insulin-transferrin-selenium with linoleic acid (ITS+1). Culture dishes (~58 cm$^2$) were coated with rat fibronectin for 30 minutes at 37° C. or for 60 minutes at room temperature. In order to inhibit initiation of differentiation, intercellular contact was prevented. Therefore, every 48 hours, MAPC were trypsinized (0.25 or 0.05% trypsin), centrifuged at 2100 RPM for 6.5 minutes, counted and replated at ~300 cells/cm$^2$.

2. Quality Control of Undifferentiated Rat MAPCs

On a regular basis, cytogenetics, Oct4 level (mRNA and staining) and phenotype of the undifferentiated cells were determined and their multilineage capacity was tested.

3. In Vitro Differentiation of MAPCs 3.1 Initiation of In Vitro Hepatic Differentiation Undifferentiated MAPCs were expanded at large scale until several million cells were obtained. Cells then were plated at 50,000-60,000 cells/cm$^2$ in Matrigel (2%) coated wells. Initially, cells were cultured in expansion medium until they reached 80-90% confluency 16 hours later. Then, cells were washed twice with PBS and the medium was switched to differentiation medium. Basal differentiation medium consisted of DMEM (60%), MCDB (40%), ascorbic acid ($1\times$), penicillin/streptomycin ($1\times$), beta-mercaptoethanol, ITS ($0.25\times$), LA-BSA ($0.25\times$) and dexamethasone ($10^{-6}$M).

3.2 Choice of Recombinant Cytokines and Medium Components

Understanding the molecular signals favoring liver development is essential for the development of a logical in vitro differentiation protocol to modulate stem cell differentiation towards the hepatic fate. With this in mind, different cytokines at variable concentrations and chronological orders were investigated for their hepatocyte inducing capacity in rMAPCs. Cytokines tested included Nodal, its co-receptor Cripto, ActivinA, Wnt3a, BMP4, bFGF, aFGF, FGF8b, EGF, Nicotinamide, heparan sulphate proteoglycan, Oncostatin M, HGF and Follistatin. All cytokines were purchased from R&D, Minneapolis, USA. Apart from the cytokines, medium components also play an important role in guiding cells towards a specific fate. The effect of changing the percentage of serum, concentration of dexamethasone (none, $5\times10^{-8}$ M and $10^{-6}$ M) and insulin was tested. Control samples consisted of rMAPCs without the addition of cytokines according to the standard protocol.

4. qRT-PCR

Total RNA was extracted using the Qiagen mini-kit. Next, samples were treated with Turbo DNAse free (Ambion, USA) for 30 minutes at 37° C. One µg of RNA was used for each cDNA-synthesis using Superscript III reverse transcriptase (Invitrogen, USA). Semiqualitative PCR was performed with Sybr Green (Invitrogen, USA) on the Eppfendorf realtime PCR machine (40 cycles). As controls, fetal (ED15), mature total liver, spleen or universal RNA were used, depending upon the markers tested. GAPDH was applied as a housekeeping gene. Results were shown in delta CT=CT (marker of interest)−CT (GAPDH) and were compared to the delta CT of the undifferentiated cells and the positive control. The lower the delta CT, the higher the expression of that gene.

5. Immunohistochemistry

Cultured cells were fixed with 4% paraformaldehyde for 10 minutes at room temperature. The following antibodies were used: Dako Rabbit anti-Albumin (A0001, 1:2000 dilution), ICN Rabbit anti-Albumin (55711, 1:10000 dilution), Chemicon Mouse anti-CK18 (CBL177, 1:10 dilution), Santa Cruz Rabbit anti-HNF1 (sc-8986, 1:50 dilution), NeoMarkers Rabbit anti-alpha-fetoprotein (RB-365A, 1:300 dilution) and Chemicon Rabbit anti-von Willebrandt factor (AB7356, 1:200). After incubation with the primary antibodies, samples were labeled with EnVision+Horseradish peroxidase (K4002 anti-Rabbit or K4000 anti-Mouse). Staining was completed with an incubation of DAB substrate-chromogen. Antibodies were titrated using primary rat hepatocytes or paraffin embedded normal rat liver. Negative controls included isotype controls used at the same concentration as the primary antibodies.

6. Funtional Assays a. Glycogen staining. Cells were fixed with methanol at −20° C. for 10 minutes and periodic acid staining was performed using a Sigma kit.

b. Albumin was measured in the medium every 48 hours beginning at day 10 of differentiation, using competitive ELISA Protocol with rat and mouse specific antibodies, following the manufacturers instructions (Bethyl).

c. Capacity to conjugate bilirubin was investigated by adding unconjugated bilirubin-BSA (50 µM-100 µM) to the medium. After different time points (0-24 hours), medium was collected to measure bilirubin mono- and di-glucuronide with high performance liquid chromatography (HPLC).

d. Electron Microscopy. A minimum of 3 million cells were collected by scraping of the cells with collagenase or dispase, centrifuged and fixed in electron microscopy-specific fixing medium. Samples were further analyzed by Prof. R. Devos, KU Leuven.

e. LDL-uptake (Biomedical Technologies, Inc). Cells were preincubated with fresh DMEM for 1 hour. Dil-Ac-LDL at a final concentration of 10 µg/ml was added to the cells for 1 to 4 hours at 37° C. Afterwards, cells were washed three times with PBS and fixed to visualize cellular LDL uptake with immunofluorescence.

f. Urea Assay. Cells were incubated with ammonium chloride (2.5 to 5 µM) for 4-6 hours and urea concentrations were screened by a colorimetric assay (Gentaur).

g. Lectin staining. Cells were fixed with 4% para-formaldehyde and blocked with TBS/1% BSA for 1 hour, incubated with lectin from Bandeiraea simplicifolia at 10 µg/ml (Sigma) and washed with TBS 3 times. Then, streptavidine-PE (BD Pharmingen) was added for 45 minutes.

h. CYP3A4 activity by testosterone hydroxylation. Cells were incubated in differentiation medium containing 25 µM rifampcin for 48 hours and the CYP3A4 substrate testosterone was added to a final concentration of 100 µM in the presence or absence of 10 µM ketoconozole, a CYP3A4 inhibitor. After a further 24 hours culture, the medium was collected and CYP3A4 activity was measured using HPLC for the production of 6β-OH testosterone. For all of the experiments described, mature rat hepatocytes or rat liver tissue served as a positive control.

II. Results

1. Characterization of Undifferentiated rat MAPCs

One subclone of rat MAPCs expresses high levels of the pluripotent marker Oct4 both at the mRNA and protein level. In addition, a micro-array analysis of this subclone showed the expression of Sal14. In contrast to embryonic stem cells, however, no Nanog or Sox2 was expressed. Undifferentiated high Oct4-expressing MAPCs express early mesendodermal markers, but no expression of mature hepatic markers such as albumin, alpha1-antitrypsin or tyrosine aminotransferase. FACS analysis showed that rat MAPCs were positive for the surface marker CD31 and negative for the mesenchymal marker CD44.

2. Differentiation of Rat MAPCs and Mouse ES Cells.

2.1 Choice of Cytokines and Medium Components

Among the large number of differentiation protocols (>200) tested, the optimal protocol was selected based upon mRNA expression levels of albumin, alpha-fetoprotein, transthyretin, tyrosine aminotransferase and alpha-1 antitrypsine. In the final 21 day differentiation protocol, a standard protocol of four sequential combinations of cytokines were used: (1) 50 ng/ml Wnt3a and 100 ng/ml ActivinA; (2) 10 ng/ml bFGF and 50 ng/ml BMP4; (3) 50 ng/ml aFGF, 10 ng/ml FGF4 and 25 ng/ml FGF8b; and (4) 20 ng/ml HGF and 100 ng/ml Follistatin (FIG. 1). In order to discriminate between hepatocyte- or biliary-like cells, Activin is inhibited by Follistatin. To verify whether the addition of the cytokines had a real hepatocyte inducing effect, differentiation was performed using basal differentiation medium only. A high concentration of dexamethasone was used because some hepatocyte specific genes (i.e., tyrosine aminotransferase, MRP2 and tryptophan 2,3 dioxygenase) are upregulated by glucocorticoids, as they contain a glucocorticoid response element. In the complete absence of serum, cell death occurred. However, using Wnt3a, differentiation was induced in serum-free conditions. If no cytokines were added to the basal differentiating medium, 2% serum was added until day 12 and then stopped. Because high concentrations of dexamethasone, together with insulin, can induce adipogenesis, a lower amount of insulin was used.

2.2 Morphology

Figure 2:
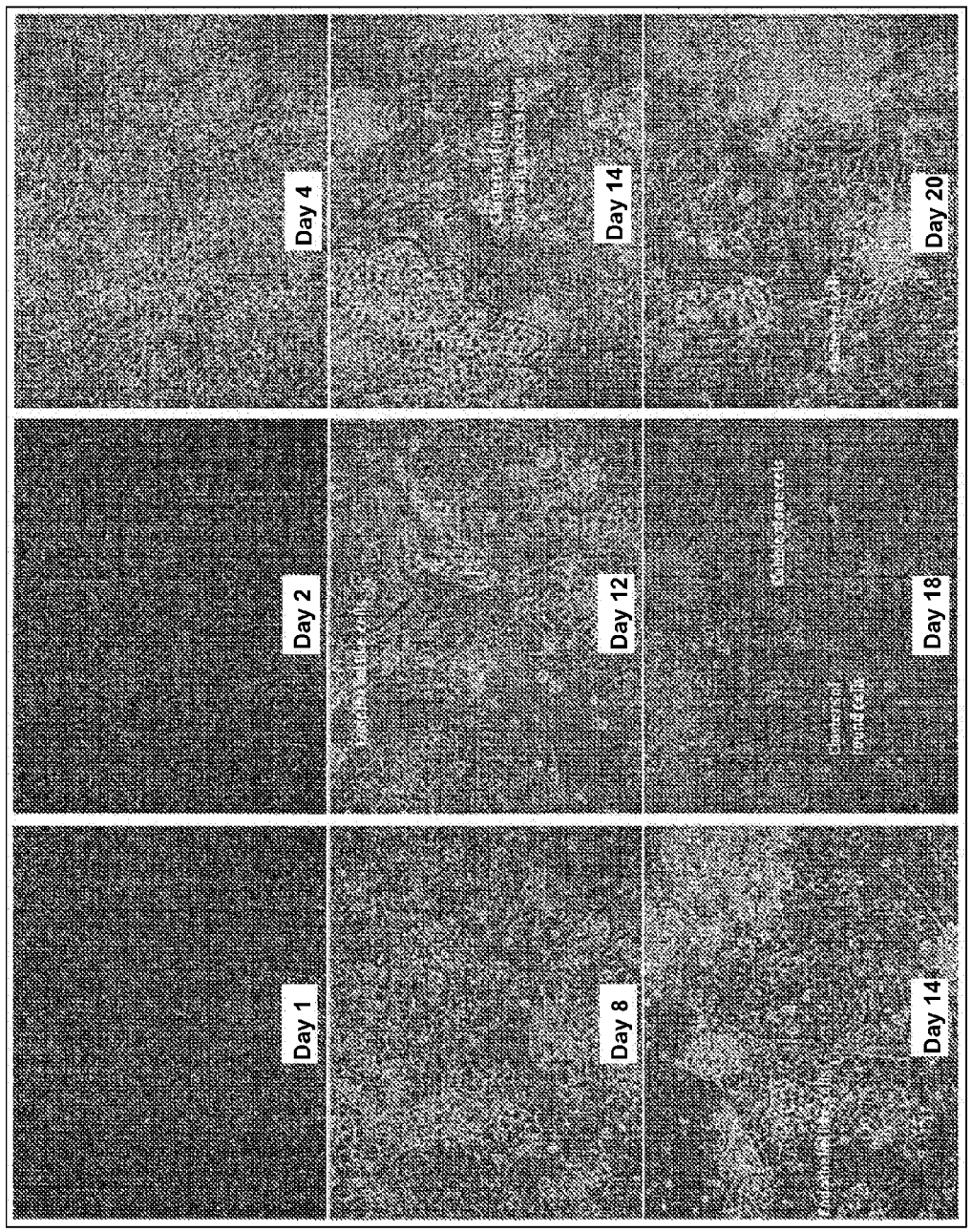
FIG. 2 are light micrographs showing an overview of the changes in morphology of differentiating HO-rMAPCs at different timepoints of differentiation.

Using light microscopy, an overview of the changes in morphology of differentiating HO-rMAPC can be seen in FIG. 2. The top three panels show the changes in morphology after days 1, 2 and 3 of differentiation, respectively. The middle three panels show the changes in morphology after days 8, 12 and 14 of differentiation, respectively. The bottom three panels show the changes in morphology after days 14, 18 and 20 of differentiation, respectively. After days 12 and 14, endothelial-like cells can be seen. Clusters of rounded cells can be seen after days 14 and 18. Cobble stone-epithelial like cells can be seen after day 18. After day 20, flattened, polygonal cells can be seen.

Figure 3:
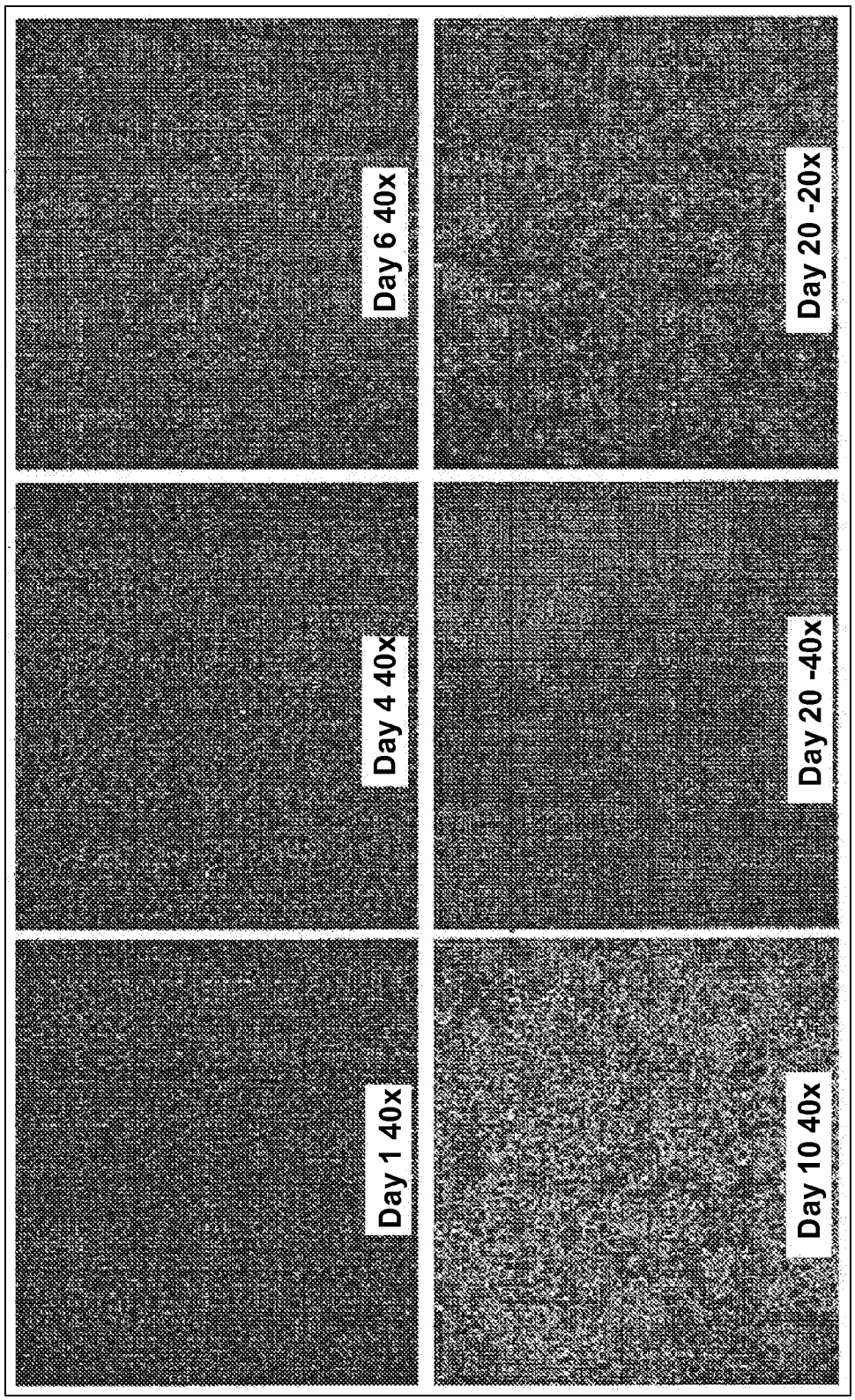
FIG. 3 are light micrographs showing the morphological changes observed during differentiation of rMAPC in differentiation medium without cytokine supplementation and changes in morphology of differentiating HO-rMAPCs.

FIG. 3 shows, using light microscopy, the morphological changes observed during differentiation of rMAPC-1 in differentiation medium without cytokine supplementation (control samples). The top three panels show the morphological changes after days 1, 4 and 6 of differentiation. The bottom three panels show the morphological changes after day 10, day 20 at 40× and day 20 at 20×, respectively, of differentiation. Overall, cells appeared morphologically more homogeneous until day 20 compared to the cytokine-containing differentiation cultures. Colonies of small rounded cells also could be seen from day 15 on, similar to cells treated with the standard protocol. Using the same cytokines, a similar heterogeneity is seen in differentiating mouse ES cells (data not shown).

Figure 4C:
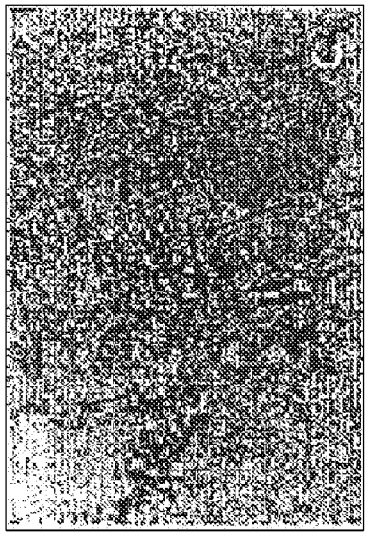
FIG. 4 A-F are electron micrographs showing characteristics of fully differentiated HO-rMAPCs.
Figure 4F:
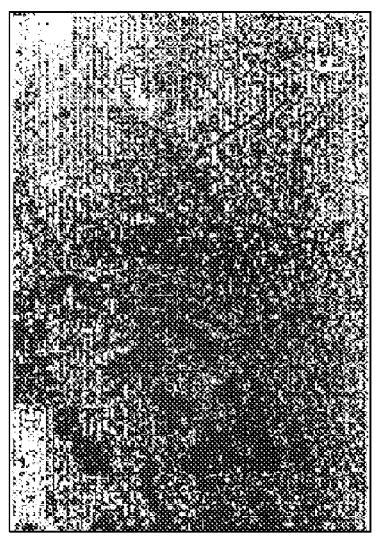
Figure 4B:
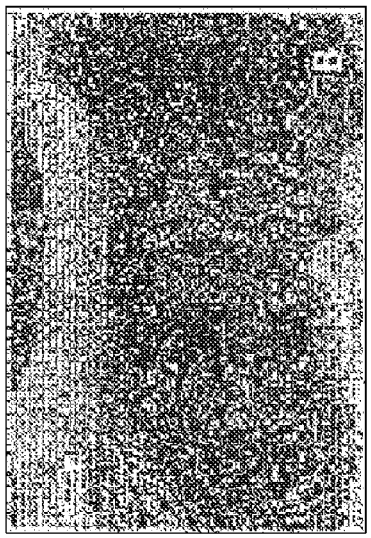
Figure 4E:
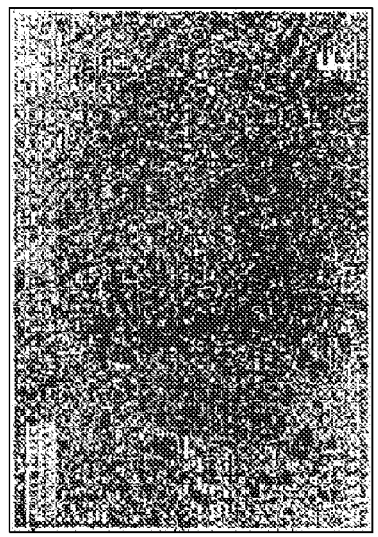
Figure 4A:
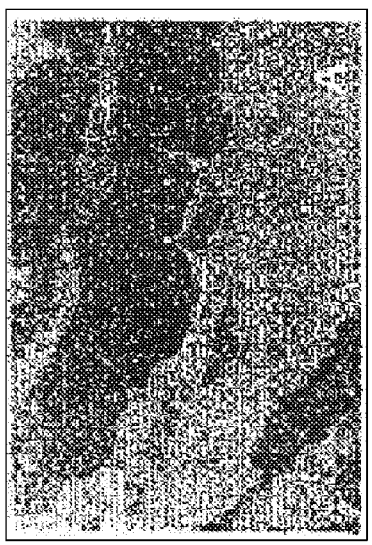
Figure 4D:
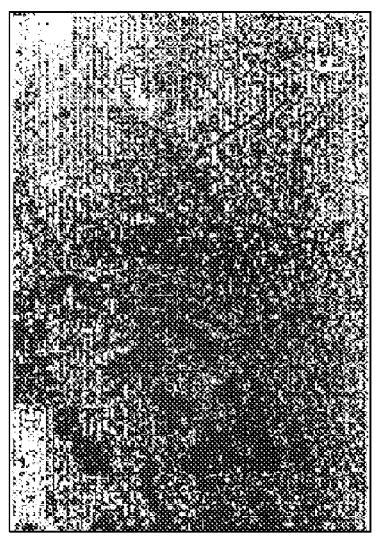

Using electron microscopy, some cells showed characteristics of both cholangiocyte-like and hepatocyte-like cells: bile duct-like structures (FIG. 4A-B); tonofilaments (FIG. 4C at arrow); polarized hepatocyte-like cells (FIG. 4D); metabolically active cells with much mitochondria FIG. 4E at arrow); and tight junctions (FIG. 4F at arrow).

2.3 qRT-PCR Results on Differentiating Rat MAPCs

Results of the qRT-PCR analysis showed the expression of specific genes over time in two different clones of rMAPCs, as shown in Tables 1a and 1b.

TABLE 1a

| | rat clone 19 | | | | |
|---|---|---|---|---|---|
| | d 0 | d 6 | d 10 | d 14 | d 20 |
| Oct4 | 5.9 +/− 1.0 (3) | 14.8 +/− 1.5 (3) | 13.4 +/− 2.5 (3) | 8.3 +/− 1.1 (3) | 12.1 +/− 3.9 (3) |
| Mixl1 | 21.6 +/− 1.2 (3) | 6.2 +/− 1.6 (3) | 11.3 +/− 1.1 (3) | 16.4 +/− 0.4 (3) | 21.2 +/− 1.7 (3) |
| Eomes | 8.5 +/− 0.2 (3) | 4.5 +/− 0.2 (3) | 8.0 +/− 0.5 (3) | 9.9 +/− 1.0 (3) | 10.1 +/− 0.2 (3) |
| Brachyury | 23.6 +/− 0.1 (3) | 18.1 +/− 3.0 (3) | 18.8 +/− 1.1 (3) | 14.7 +/− 0.8 (3) | 19.2 +/− 2.0 (3) |

TABLE 1a-continued

| | rat clone 19 | | | | |
|---|---|---|---|---|---|
| | d 0 | d 6 | d 10 | d 14 | d 20 |
| Tm4sf2 | 21.7 +/− 1.8 (3) | 3.2 +/− 0.4 (3) | 6.4 +/− 1.1 (3) | 7.5 +/− 0.4 (3) | 9.1 +/− 0.4 (3) |
| Sox17 | 4.7 +/− 1.1 (2) | 7.7 +/− 0.7 (2) | 7.3 +/− 0.0 (2) | 6.6 +/− 0.7 (2) | 6.7 +/− 1.5 (2) |
| Foxa2 | 6.9 +/− 0.1 (2) | 5.6 +/− 0.2 (2) | 5.6 +/− 0.3 (2) | 5.5 +/− 0.3 (2) | 7.0 +/− 0.1 (2) |
| CXCR4 | 17.5 +/− 0.7 (3) | 5.3 +/− 1.3 (3) | 8.6 +/− 0.8 (3) | 9.8 +/− 0.7 (3) | 8.6 +/− 1.6 (3) |
| Flk1 | 19.5 +/− 1.6 (3) | 19.4 +/− 1.2 (3) | 17.2 +/− 2.3 (3) | 12.5 +/− 0.6 (3) | 12.2 +/− 0.9 (3) |
| E-cadherin | 5.8 (1) | 1.9 (1) | 1.9 (1) | 2.1 (1) | 2.5 (1) |
| Hex1 | 8.7 +/− 0.0 (2) | 4.2 +/− 0.5 (2) | 5.4 +/− 0.1 (2) | 5.8 +/− 0.1 (2) | 6.9 +/− 0.3 (2) |
| Prox1 | 8.7 +/− 0.4 (3) | 5.2 +/− 0.7 (3) | 4.8 +/− 0.2 (3) | 5.0 +/− 0.5 (3) | 5.4 +/− 0.4 (3) |
| HNF1a | 11.6 +/− 1.1 (3) | 8.2 +/− 0.9 (3) | 8.3 +/− 1.9 (3) | 7.8 +/− 0.8 (3) | 7.7 +/− 1.2 (3) |
| HNF4a | 13.3 +/− 0.8 (3) | 7.0 +/− 0.5 (3) | 6.1 +/− 0.0 (3) | 7.7 +/− 1.4 (3) | 6.9 +/− 1.9 (3) |
| HNFβa | 17.4 +/− 0.8 (3) | 7.8 +/− 1.1 (3) | 5.0 +/− 1.3 (3) | 5.5 +/− 0.5 (3) | 4.5 +/− 1.0 (3) |
| C/EBPa | 7.9 +/− 0.4 (3) | 5.8 +/− 0.3 (3) | 6.1 +/− 0.4 (3) | 6.0 +/− 0.0 (3) | 5.0 +/− 1.3 (3) |
| AFP | 21.2 +/− 2.4 (4) | 2.0 +/− 0.7 (4) | 0.8 +/− 0.7 (4) | 0.8 +/− 0.9 (4) | 1.5 +/− 0.8 (4) |
| TTR | 16.7 +/− 1.8 (3) | 2.8 +/− 1.2 (3) | 0.6 +/− 1.9 (3) | 1.8 +/− 1.2 (3) | 1.5 +/− 1.8 (3) |
| CK19 | 8.8 +/− 0.6 (3) | 5.0 +/− 0.2 (3) | 4.7 +/− 0.6 (3) | 3.1 +/− 0.7 (3) | 3.4 +/− 0.5 (3) |
| Alb | 19.4 +/− 1.4 (4) | 11.0 +/− 0.6 (4) | 6.5 +/− 0.2 (4) | 2.0 +/− 0.4 (4) | 2.0 +/− 0.8 (4) |
| CK18 | 3.9 +/− 1.1 (3) | 1.3 +/− 0.2 (3) | 0.1 +/− 1.1 (3) | 1.0 +/− 0.5 (3) | 0.4 +/− 1.4 (3) |
| AAT | 22.5 +/− 1.1 (3) | 9.4 +/− 2.1 (3) | 3.1 +/− 0.6 (3) | 2.4 +/− 0.4 (3) | 1.9 +/− 0.6 (3) |
| TAT | 22.9 +/− 0.9 (3) | 16.2 +/− 0.8 (3) | 10.6 +/− 0.3 (3) | 6.6 +/− 0.4 (3) | 6.1 +/− 0.4 (3) |
| G6P | 23.7 +/− 1.1 (3) | 19.3 +/− 1.2 (3) | 17.3 +/− 0.4 (3) | 12.3 +/− 1.6 (3) | 13.2 +/− 0.9 (3) |
| Cx32 | 23.3 +/− 0.4 (3) | 22.3 +/− 0.1 (3) | 15.7 +/− 2.2 (3) | 14.0 +/− 1.9 (3) | 13.3 +/− 0.9 (3) |
| PEPCK | 21.5 +/− 1.5 (3) | 13.9 +/− 0.3 (3) | 15.0 +/− 0.7 (3) | 16.1 +/− 1.1 (3) | 14.9 +/− 0.7 (3) |
| CYP7A1 | 23.9 +/− 0.5 (3) | 18.5 +/− 1.5 (3) | 19.3 +/− 1.9 (3) | 20.8 +/− 2.5 (3) | 22.5 +/− 1.7 (3) |

TABLE 1b

| | Rat Clone R2Old rMAPC-1 | | | | |
|---|---|---|---|---|---|
| | d 0 | d 6 | d 12 | d 16 | d 20 |
| Oct4 | 5.61 +/− 0.9 (11) | 10.6 +/− 2.09 (15) | 12.94 +/− 0.8 (10) | 11.36 +/− 0.9 (7) | 10.615 +/− 1.19 (11) |
| Gsc | 12.9 +/− 1.4 (10) | 6.3 +/− 1.9 (17) | 14.92 +/− 1.2 (10) | 13.35 +/− 1.08 (6) | 15.84 +/−1.13 (7) |
| Tm4sf2 | 18.19 +/− 2.8 (6) | 2.6 +/− 0.9 (10) | 6.68 +/− 0.35 (6) | 7.97 +/− 1.19 (3) | 7.27 +/− 0.8 (6) |
| Mixl1 | 18.566 +/− 0.5 (5) | 7.5 +/− 2 (7) | 15.27 +/− 0.48 (5) | 19.09 +/− 0.4 (2) | 16.96 +/− 2.1 (5) |
| eomes | 8.66 +/− 0.98 (6) | 3.7 +/− 1.4 (9) | 9.2 +/− 0.7 (5) | 9.9 +/− 0.1 (2) | 9.44 +/− 0.3 (4) |
| brachyuri | ND | ND | ND | ND | ND |
| Lhx | 11.17 +/− 0.4 (6) | 3.6 +/− 1.09 (6) | 9.96 +/− 0.7 (4) | 12.69 +/− 0.08 | 12.43 +/− 1.4 (4) |
| Sox7 | 6.7 +/− 2.1 (9) | 6.16 +/− 1.47 (13) | 6.63 +/− 0.3 (7) | 7.8 +/− 2.5 (5) | 9.3 +/− 3 (8) |
| Sox17 | 2.5 +/− 1.35 (6) | 3.17 +/− 1.9 (8) | 5.8 +/− 0.9 (4) | 8.53 +/− 0.2 (2) | 7.3 +/− 2 (4) |
| Tmprss2 | 12.7 +/− 0.4 (4) | 2.6 +/− 0.4 (7) | 2.4 +/− 0.5 (5) | 3.38 +/− 0.14 (2) | 2.77 +/− 0.17 (4) |
| Foxa2 | 4.5 +/− 0.5 (4) | 9.04 +/− 0.8 (4) | 3.5 +/− 0.2 (4) | 4.46 +/− 0.9 4) | 4.4 +/− 0.5 (6) |
| Cxcr4 | 15.77 +/− 1.76 (9) | 5.9 +/− 1.5 (816) | 9.36 +/− 0.9 (9) | 9.8 +/− 1.04 | 9.3 +/− 0.6 (7) |
| FlK1 | 19.9 +/− 2 (5) | 16.07 +/− 1.8 (7) | 11.31 +/− 2.65 (8) | 11.24 +/− 2.1 (5) | 9.6 +/− 1.6 (7) |
| E-cadherin | ND | ND | ND | ND | ND |
| Hex1 | 8.9 +/− 0.4 (4) | 3.83 +/− 0.4 (8) | 4.2 +/− 0.8 (6) | 5.3 +/− 0.2 (4) | 5.77 +/− 0.4 (8) |
| Prox1 | 9.167 +/− 0.4 (5) | 5.3 +/− 0.8 (8) | 4.29 +/− 1.3 (8) | 5.5 +/− 1.6 (4) | 4.86 +/− 0.9 (8) |
| Hnf1a | 11.55 +/− 0.5 (6) | 8.32 +/− 0.7 (8) | 7.79 +/− 0.7 (7) | 8.05 +/− 0.4 (6) | 7.78 +/− 0.5 (12) |
| Hnf1b | 6.86 +/− 1.1 (5) | 6.68 +/− 0.9 (8) | 6.37 +/− 1.15 (5) | 7.07 +/− 0.8 (4) | 7.03 +/− 0.6 (12) |
| Hnf6 | 17.02 +/− 2 (5) | 9.19 +/− 1.4 (8) | 5.27 +/− 1.2 (8) | 4.87 +/− 0.2 (4) | 5.22 +/− 0.8 (12) |
| Cebpa | 8.14 +/− 1.15 (5) | 5.87 +/− 0.9 (8) | 0.66 +/− 0.6 (6) | 6.57 +/− 0.5 (4) | 5.72 +/− 0.3 (8) |
| Hnf4a | 15.19 +/− 1.46 (5) | 6.24 +/− 0.8 (7) | 7.67 +/− 1.7 | 6.018 +/− 1.3 (5) | 6.96 +/− 1.5 (6) |
| AFP | 21.07 +/− 2.2 (4) | 5.17 +/− 2 (20) | 0.01 +/− 0.76 (15) | 0.4(neg) +− 9.02 (6) | 0.2(neg) +/− 0.76 (12) |
| TTR | 15.5 +/− 0.9 (4) | 2.89 +/− 1.3 (18) | 0.32 +/− 0.63 (15) | 0.4 +/− 0.9 (6) | 0.3 +/− 0.6 (12) |
| CK19 | 7.42 +/− 0.2 (7) | 3.8 +/− 0.5 (8) | 3.1 +/− 0.5 (8) | 3.727 +/− 0.5 (4) | 1.87 +/− 0.15 (8) |
| Alb | 21.01 +/− 2.7 (19) | 13.94 +/− 1.2 (17) | 8.9 +/− 1.7 (14) | 6.24 +/− 1.55 (7) | 1.14 +/− 1.8 (20) |
| CK18 | 0.8 +/− 2.15 (4) | 0.8(neg) +/− 0.6 (9) | 0.57 +/− 0.3 (7) | 0.85 +/− 0.4 (5) | 0.7 +/− 0.2 (6) |
| AAT | 20.04 +/− 2.9 (10) | 9.94 +/− 3.6 (15) | 2.6 +/− 0.5 (11) | 0.76 +/− 1.15 (7) | 1.3 +/− 1.03 (18) |
| TAT | 21.47 +/− 2 (10) | 13.07 +/− 2.3 (16) | 9.3 +/− 1.7 (14) | 7.4 +/− 0.8 (7) | 4.3 +/− 1.07 (30) |
| G6P | 23.06 +/− 1 (10) | 16.5 +/− 1.6 (15) | 16.07 +/− 1.8 (13) | 14.63 +/− 1.3 (10) | 11.38 +/− 1.07 (25) |
| Cx32 | 22.88 +/− 0.8 (10) | 19.7 +/− 3 (13) | 15.89 +/− 2.6 (12) | 13.62 +/− 0.8 (12) | 12.8 +/− 0.9 (25) |
| PepcK | 22.48 +/− 0.9 (4) | 12.95 +/− 2 (4) | 14.08 +/− 1.2 (4) | 12.6 +/− 1.2 (2) | 11.29 +/− 1 (14) |
| Cyp7a1 | 23.21 +/− 2.17 (6) | 19.75 +/− 2.2 (5) | 16.9 +/− 1.2 (5) | 17.05 +/− 0.1 (3) | 16.5 +/− 1.9 (15) |
| Mrp2 | 19.84 +/− 2.17 (8) | 15.02 +/− 1.4 (11) | 12.63 +/− 2 (11) | 11.53 +/− 2.1 (8) | 10.7 +/− 1.5 (18) |
| Bsep | 22.3 +/− 1.8 (8) | 18.08 +/− 2.2 (10) | 16.69 +/− 1.1 (7) | 15.35 +/− 0.5 (8) | 13.2 +/− 1.4 (22) |
| Arg1 | 14.79 +/− 0.8 (7) | 9.28 +/− 0.7 (9) | 7.8 +/− 0.7 (10) | 8.01 +/− 1.35 (8) | 8.06 +/− 0.9 (22) |

From these studies, the following conclusions were drawn:

a. Differentiation of MAPCs performed in the presence of the different cytokines, in the order in which they are added to the medium, yielded a final population of cells that expressed more mature hepatic transcripts compared with MAPCs maintained in the absence of cytokines but in same medium and at similar density. For some endodermal genes, such as AFP and TTR, expression increased earlier in the multi-step protocol. The slighter upregulation of hepatic specific genes, even in the absence of cytokines, suggested that cell-cell contact is important to initiate the endodermal differentiation process.

b. As a morphological heterogeneous cell population was obtained, expression of non-endodermal markers was evaluated. Also found were genes expressed in endothelium (Flk1, PECAM) and a transient upregulation of smooth muscle transcripts (SM 22, calponin, SM actin). Expression of these non-hepatic transcripts was more similar between the two culture conditions.

c. During the first days of differentiation, Oct4 expression was downregulated. On day 6, there was a transient upregulation of definitive endoderm specific transcripts, such as goosecoid and CXCR4. As in normal liver development, expression of these genes decreased again upon further maturation. Over time, slight down-regulation of the primitive endodermal marker Sox 7 was observed.

d. A high concentration of dexamethasone and a low concentration of insulin resulted in enhanced expression of some mature markers (albumin, TAT).

Abbreviation of the markers and the positive control used for each marker is shown in Table 2.

TABLE 2

| ABBREVIATION | ABBREVIATION FOR | POSITIVE CONTROL |
|---|---|---|
| Alb | Albumin | Fetal liver E15 |
| AAT | Alpha1-antitrypsin | Fetal liver E15 |
| TAT | Tyrosine aminotransferase | Adult rat liver |
| MRP2 | Multidrug resistant protein 2 | Fetal liver E15 |
| NTCP | Na+/taurocholate-cotransporting polypeptide | Fetal liver E15 |
| DPPIV | Dipeptidyl-peptidase 4 | Fetal liver E15 |
| CX32 | Connexin 32 | Fetal liver E15 |
| GLY S | Glycogen Synthase 1 | Fetal liver E15 |
| TRYPT | Tryptophan 2,3-dioxygenase | Fetal liver E15 |
| ARG1 | Arginase type 1 | Fetal liver E15 |
| G6P | Glucose-6-phosphatase | Fetal liver E15 |
| CYP7A1 | Cholesterol 7 α-hydroxylase | Fetal liver E15 |
| PK LIVER | Liver specific pyruvate kinase | Fetal liver E15 |
| F VII | Factor VII | Fetal liver E15 |
| TTR | Transthyretin or pre-albumin | Fetal liver E15 |
| AFP | Alpha-fetoprotein | Fetal liver E15 |
| CXCR4 | Chemokine receptor 4 | Fetal liver E15 |
| HNF1 | Hepatocyte nuclear factor 1 | Fetal liver E15 |
| HNF4a | Hepatocyte nuclear factor 4 α | Adult rat liver |
| CK19 | Cytokeratin 19 | Fetal liver E15 |
| CEBPa | CCAAT enhancer-binding protein alpha | Fetal liver E15 |
| FOXH1 | forkhead box H1 = FAST | Fetal liver E15 |
| FGF8 | Fibroblast growth factor 8 | Fetal liver E15 |
| GSC | Goosecoid | Fetal liver E15 |
| SOX7 | SRY-related HMG box proteins 7 | Fetal liver E15 |
| CL18 | Cytokeratin 18 | Fetal liver E15 |
| HEX | Hematopoietically expressed homeobox | Fetal liver E15 |
| HNF3B | Hepatocyte nuclear factor 3B | Fetal liver E15 |
| C-MET | HGF-receptor | Fetal liver E15 |
| CK8 | Cytokeratin 8 | Fetal liver E15 |
| GATA4 | GATA family of zinc finger-containing transcription factors | Fetal liver E15 |
| PROX1 | prospero-related homeobox 1 | Fetal liver E15 |
| PDX1 | Pancreas Duodenum Homeobox-1 | Fetal liver E15 |
| SM22 | Smooth muscle 22 | Universal RNA |
| CALPON | Calponin | Universal RNA |
| S M ACT | Smooth muscle actin | Universal RNA |
| FLK1 | VEGF-receptor-2 | Universal RNA |
| PECAM | platelet/endothelial cell adhesion molecule-1/CD31 | Universal RNA |
| NKX2.5 | Early cardiac specific transcription factor NK2 transcription factor related, locus 5 | Universal RNA |
| GATA6 | GATA family of zinc finger-containing transcription factors | Universal RNA |

TABLE 2-continued

| ABBREVIATION | ABBREVIATION FOR | POSITIVE CONTROL |
|---|---|---|
| BLBP | Brain lipid binding protein | Embryonic Brain |
| EN1 | Early forebrain marker | Embryonic Brain |
| NESTIN | intermediate filament protein central nervous system progenitor marker | Embryonic Brain |
| OTX1 | Transcription factor specific for anterior neurectoderm | Embryonic Brain |
| VIMENTIN | cytoskeleton filament expressed in mesenchymal cells afterbirth | Embryonic Brain |
| SOX2 | SRY-related HMG box proteins 2 Early neuronal marker | Embryonic Brain |
| PAX6 | Paired box gene 6; Developing eye and pancreas and distinct domains of the CNS | Embryonic Brain |
| MHC-1 | Major histocompatibility complex-1 | Universal RNA |
| OCT4 | POU transcription factor family-Pluripotency marker | Universal RNA |

2.4 Immunohistochemistry

Figure 5C:
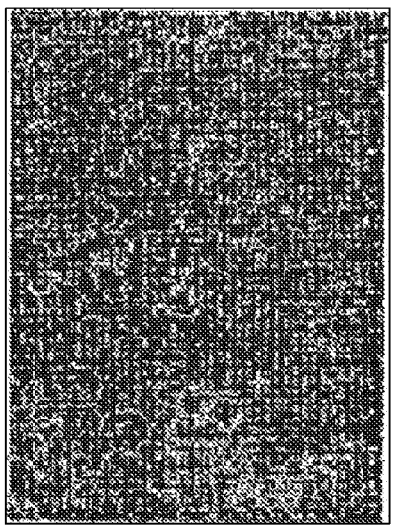
FIG. 5 A-F shows immunohistochemical staining for rAFP at different timepoints of differentiation of rMAPC: A=day 3; B=day 6; C=day 12; D=day 16; E=day 20; and F=isotype control.
Figure 5F:
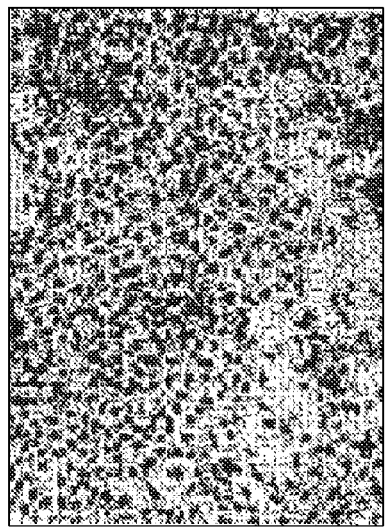
Figure 5B:
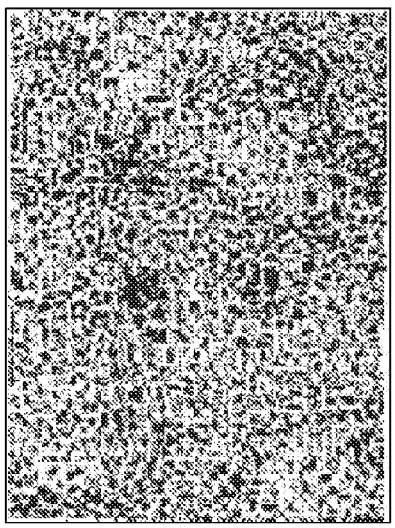
Figure 5E:
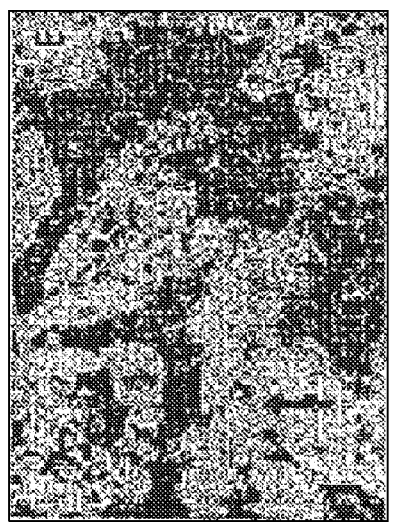
Figure 5A:
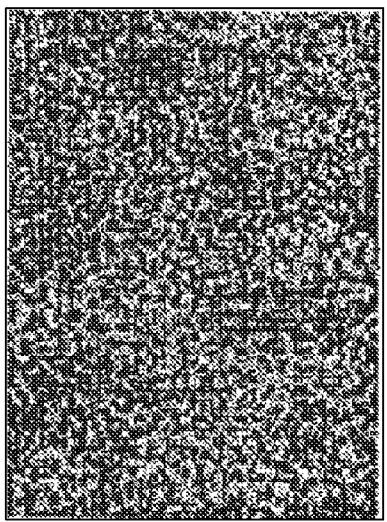
Figure 5D:
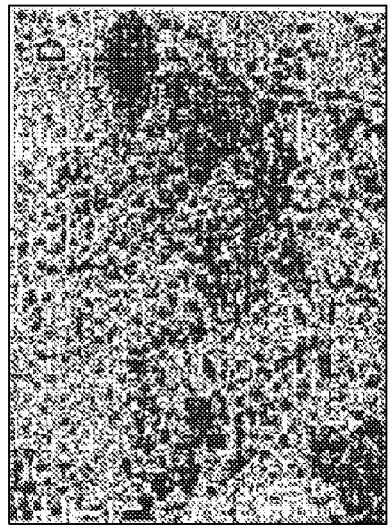

FIG. 5A-F shows immunohistochemical staining for rAFP at different timepoints of differentiation of rMAPC. FIG. 5A shows rAFP staining after day 3 of differentiation. FIG. 5B shows rAFP staining after day 6 of differentiation. FIG. 5C shows rAFP staining after day 12 of differentiation. FIG. 5D shows rAFP staining after day 16 of differentiation. FIG. 5E shows rAFP staining after day 20 of differentiation. FIG. 5F shows rAFP staining after day 20 in the isotype control.

Figure 6C:
FIG. 6 A-F shows immunohistochemical staining for rALB at different timepoints of differentiation of rMAPCs.
Figure 6B:
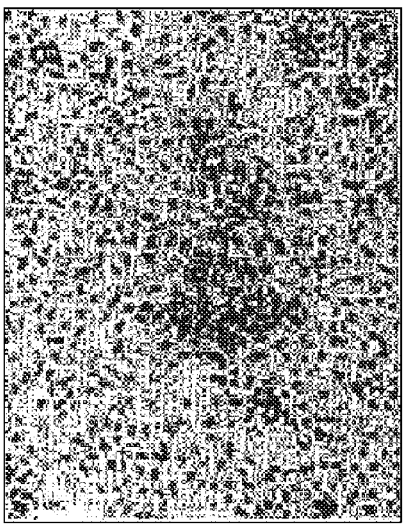
Figure 6A:
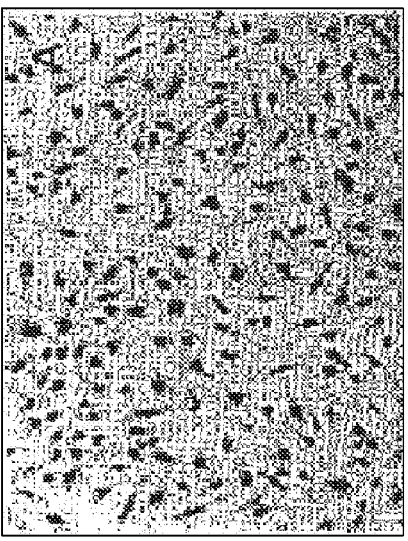
Figure 6F:
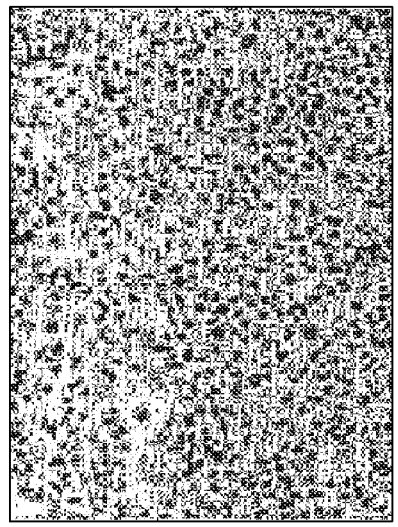
Figure 6E:
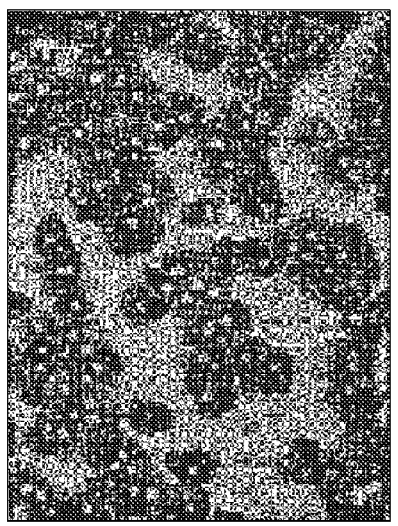
Figure 6D:
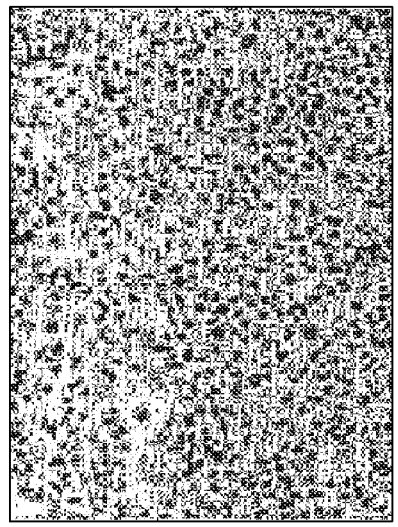

FIG. 6A-F shows immunohistochemical staining for rALB at different timepoints of differentiation of rMAPC. FIG. 6A shows rALB staining of undifferentiated rMAPC at day 0. FIG. 6B shows rALB staining after day 12 of differentiation. FIG. 6C shows rALB staining after day 16 of differentiation. FIG. 6D shows rALB staining after day 20 of differentiation. FIG. 6E shows rALB staining in rat hepatocytes. FIG. 6F shows rALB staining after day 20 in the isotype control.

Figure 7:
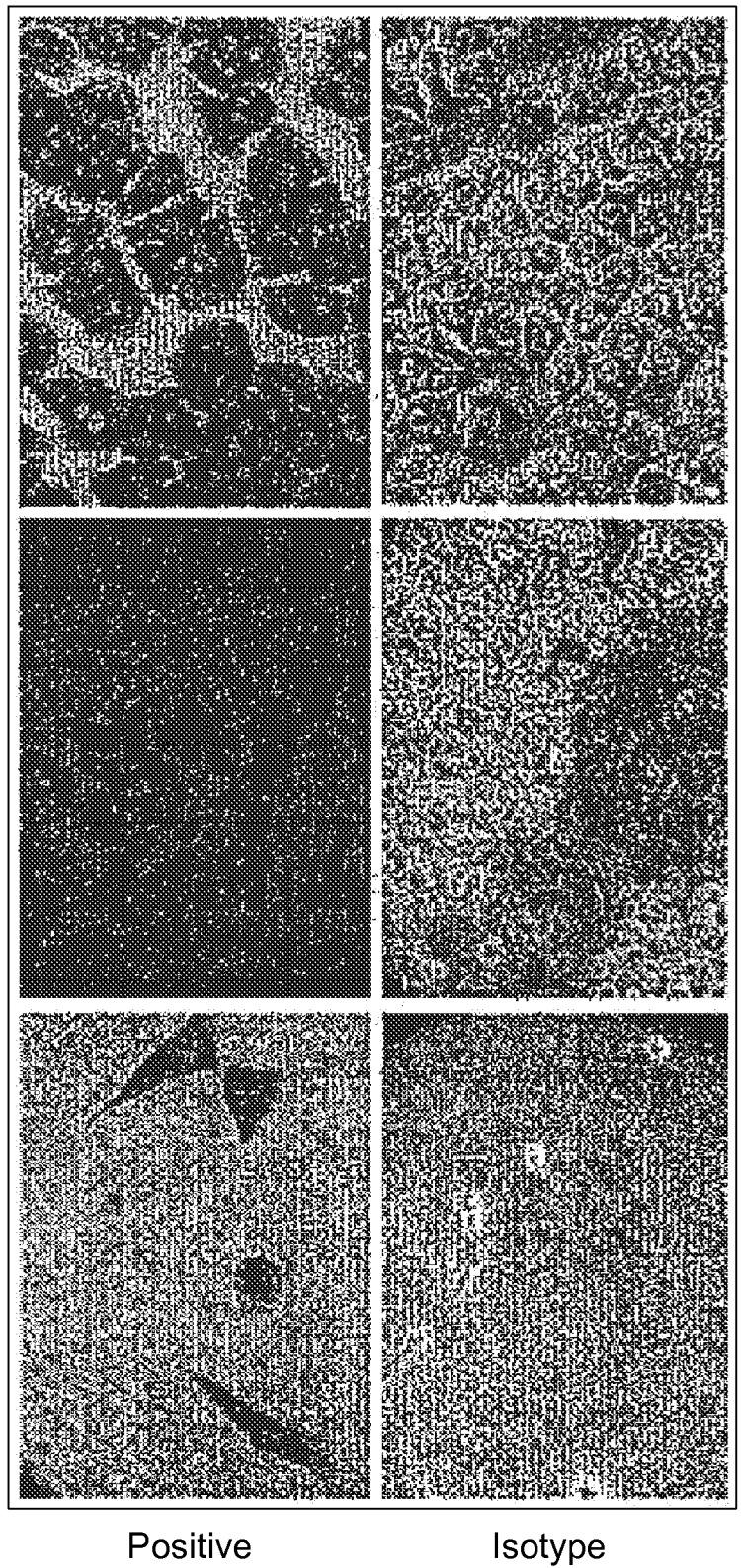
FIG. 7 shows immunohistochemical staining for CK18 at different timepoints of differentiation of rMAPCs. The top three lines are, respectively, undifferentiated rMAPC-1; after day 20; and in mature rat hepatocytes. The lower three lines show the respective isotype controls.

FIG. 7 shows immunohistochemical staining for CK18 at different timepoints of differentiation of rMAPC-1. The top three lines are, respectively, CK18 staining in undifferentiated rMAPC-1 at day 0; CK18 staining after day 20 of differentation; and CK18 staining in mature rat hepatocytes. The lower three lines show the isotype controls used at day 0, after day 20 and in mature rat hepatocytes, respectively, in the isotype control.

2.6 Functional Assays a. Secretion of Albumin in the Medium

Figure 8:
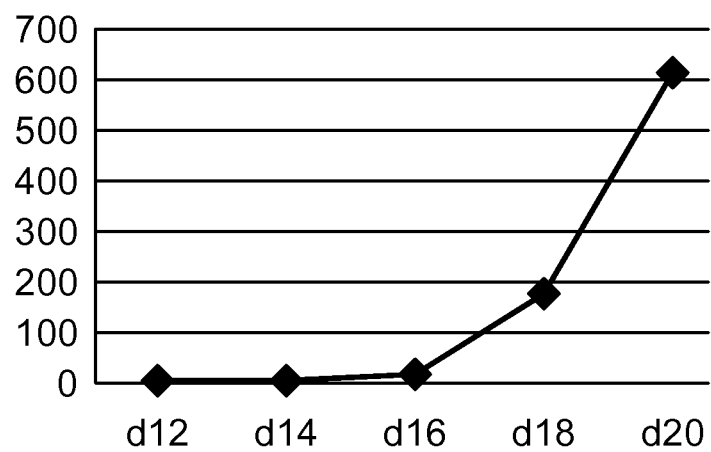
FIG. 8 is a graph illustrating the time-dependent increase of albumin concentration during hepatic differentiation of rMAPCs (mean of >10 experiments).

Using rat albumin specific ELISA, increasing amounts of albumin could be detected in the conditioned medium of differentiating rat MAPCs after days 12, 14, 16, 18 and 20 (FIG. 8). No albumin was detected in the medium of cells grown in control medium without cytokines. Decreasing the concentration of dexamethasone resulted in reduced secretion of albumin.

b. Glycogen Storage

Figure 9:
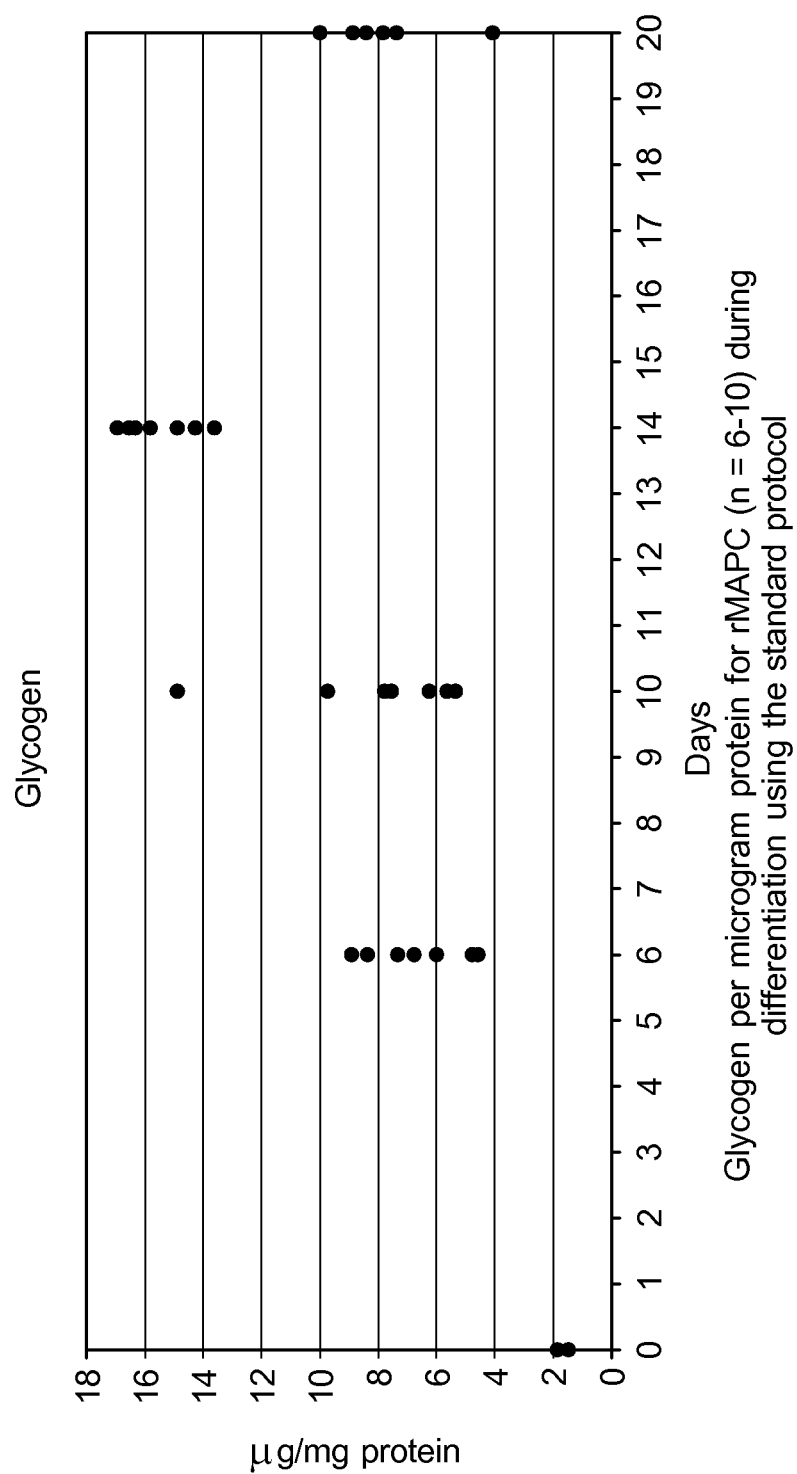
FIG. 9 is a graph illustrating glycogen storage (µg/mg protein) in rMAPC (n=6-10).

As early as day 14 of differentiation, a significant amount of cells stained positive for PAS staining. FIG. 9 shows the concentration of glycogen (μg/mg protein) for rMAPC (n=6-10).

c. LDL-Uptake

LDL-uptake is a characteristic of both endothelial cells and hepatocytes. The difference between these two cells was determined by the faster up-take of LDL by hepatocytes (2 hours) compared to endothelial cells (4 hours) (data not shown).

d. Lectin Staining

A subpopulation of cells stained positive for Lectin, which is an endothelial marker, at day 18 of differentiation, as was suggested by qRT-PCR results (data not shown). During liver embryology, contact of hepatoblasts with endothelial cells is necessary for their further maturation. Thus, the inventors hypothesized that a heterogeneous cell population, including endothelial cells, may have beneficial effects on the maturation of adjacent hepatic-like cells.

e. Conjugation of Bilirubin

In vivo, bilirubin is a degradation product of the heme moiety of hemoglobin and heme proteins such as cytochromes, muscle myoglobin and catalase. Because unconjugated bilirubin is unsoluble, it is transported as an albumin-bound complex (90%). Intrahepatic transport of unconjugated bilirubin to the endoplasmatic reticulum occurs by binding to ligandin (glutathione S-transferase B) and/or protein Z. Efficient excretion of bilirubin across the bile canaliculi requires the conversion of unconjugated bilirubin to polar conjugates by esterification of one or two propionic acid side chains of the bilirubin molecule, with a sugar, mostly glucuronic acid, to form water-soluble mono or diglucuronated bilirubin, respectively. This is done by uridine diphosphate-glucuronyltransferase 1A1. Bilirubin glucuronides are excreted into bile canaliculi by the multidrug resistance associated protein 2 (MRP2), a member of the ATP-cassette transporter family. In normal human bile, 80% of the conjugated bilirubin exists as bilirubin diglucuronide, and only a minor portion exists in the monoglucuronide state. In rats, in contrast, monoconjugated bilirubin is the major fraction.

Figure 10A:
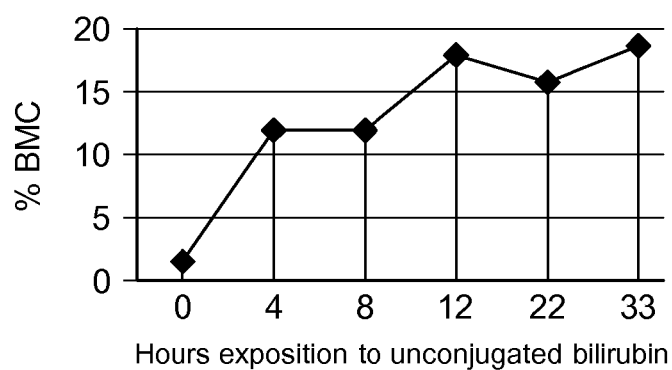
FIG. 10 A-B are graphs illustrating the increasing formation of monoconjugated bilirubin after 4, 8, 12, 22, and 33 hours in mature rat hepatocytes (A) and in differentiated rMAPC after day 20 (B). (n=3).
Figure 10B:
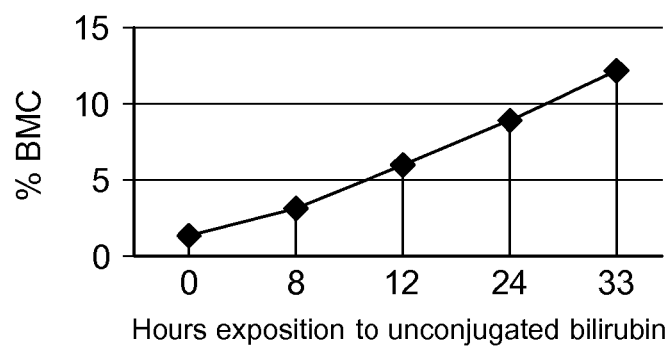

FIG. 10 shows an increasing formation of monoconjugated bilirubin after 4, 8, 12, 22 and 33 hours in mature rat hepatocytes (FIG. 10A) and in differentiated rMAPC after day 20 (FIG. 10B).

In conclusion, a 21 day differentiation protocol resulted in a heterogeneous cell population containing hepatic-like cells, but also epithelial, endothelial and smooth muscle cells. Although only a limited amount of cells were mature hepatocytes, they secreted a significant amount of albumin, took up LDL, conjugated unconjugated bilirubin towards monoglucuronated bilirubin, showed signs of glycogen storage, and, as shown using electron microscopy, their morphology was consistent with biliary and hepatic cells.

Example 2

I. Methodology

The human embryonic stem cell (hESC) line, H9, and induced pluripotent stem cell (hIPSC) were differentiated according to the standard protocol. At different time points (prior to cytokine exposure, at the three time points following exposure to the three other sets of cytokines as described herein, and the final time point representing the endpoint cell type), samples were obtained for RT-qPCR analysis of PS genes, ME/DE genes, hepatoblasts and definitive hepatocyte genes. In addition, cultures were evaluated for secretion of albumin, conversion of $NH_3$ to urea, glycogen storage, metabolization of bilirubin, GST activity, and expression of coagulation factors Factor V, Factor VII, Protein C, gamma-glutamylcarboxylase (GGCX) and Vitamin K epoxide reductase (VKOR).

II. Results

The RT-qPCR results are shown in FIG. 11 A-J. The RT-qPCr results also are shown in Table 3a-b. Table 3a and 3b provide values for expression of genes in the human ESC line H9 and the hiPS cells, respectively, as described in the methodology.

TABLE 3a

Gene Expression of Human ESC line H9
hESC (H9)

|  | d 0 | d 6 | d 10 | d 14 | d 20 |
|---|---|---|---|---|---|
| Oct4 | .−0.3 +/− 1.0 (8) | .−0.2 +/− 1.1 (12) | 3.3 +/− 1.4 (8) | 5.3 +/− 2.0 (10) | 6.4 +/− 2.1 (8) |
| Mixl1 | 8.6 +/− 1.3 (3) | 3.9 +/− 1.0 (6) | 9.5 +/− 0.4 (4) | 9.9 +/− 1.6 (4) | 9.7 +/− 2.5 (3) |
| Eomes | 10.7 +/− 2.7 (4) | 2.5 +/− 1.4 (6) | 7.0 +/− 1.4 (6) | 6.7 +/− 1.7 (4) | 15.5 +/− 2.5 (4) |
| Brachyury | 10.4 +/− 2.5 (5) | 5.9 +/− 1.3 (7) | 9.7 +/− 1.7 (3) | 12.3 +/− 1.0 (7) | 13.4 +/− 0.8 (5) |
| Tm4sf2 | 8.0 +/− 0.6 (3) | 7.0 +/− 0.7 (3) | 8.0 +/− 0.6 (3) | 9.0 +/− 0.3 (3) | 6.6 +/− 0.5 (3) |
| Sox7 | 13.1 +/− 0.5 (3) | 13.1 +/− 0.9 (3) | 9.7 +/− 1.3 (3) | 11.4 +/− 0.4 (3) | 10.5 +/− 0.4 (3) |
| Gsc | 13.2 +/− 3.9 (4) | 6.6 +/− 1.8 (6) | 12.8 +/− 2.4 (6) | 11.8 +/− 2.7 (4) | 12.7 +/− 1.6 (4) |
| Sox17 | 7.9 +/− 2.8 (4) | 4.5 +/− 2.0 (7) | 4.6 +/− 1.4 (5) | 6.5 +/− 2.0 (5) | 7.7 +/− 1.4 (4) |
| Foxa2 | 12.4 +/− 3.1 (6) | 9.5 +/− 2.4 (10) | 6.7 +/− 1.7 (6) | 9.3 +/− 3.2 (8) | 10.2 +/− 1.8 (6) |
| Cxcr4 | 6.3 +/− 2.5 (4) | 3.9 +/− 1.1 (7) | 6.4 +/− 1.4 (5) | 4.7 +/− 1.5 (5) | 6.5 +/− 1.0 (4) |
| Flk1 | 7.3 +/− 0.2 (3) | 6.9 +/− 0.2 (3) | 5.6 +/− 0.5 (3) | 6.5 +/− 0.7 (3) | 3.7 +/− 0.1 (3) |
| E-cadherin | 7.7 +/− 2.1 (7) | 10.2 +/− 3.0 (7) | 9.6 +/− 2.7 (6) | 9.6 +/− 3.5 (7) | 7.7 +/− 2.8 (7) |
| Hex1 | + | + | + | + | + |
| Prox1 | 10.0 +/− 0.5 (3) | 8.4 +/− 0.2 (3) | 6.2 +/− 0.1 (3) | 5.3 +/− 1.6 (3) | 5.8 +/− 0.5 (3) |
| HNF1a | 14.4 +/− 0.2 (3) | 13.6 +/− 1.3 (3) | 6.8 +/− 1.5 (3) | 8.7 +/− 2.0 (3) | 7.9 +/− 0.9 (3) |
| HNF4a | 11.2 +/− 3.2 (3) | 7.1 +/− 1.6 (3) | 4.1 +/− 1.8 (4) | 9.5 +/− 4.9 (3) | 2.7 +/− 0.5 (3) |
| HNF6a | 21.6 +/− 0.2 (3) | 21.0 +/− 0.9 (3) | 21.7 +/− 0.7 (3) | 21.2 +/− 0.4 (3) | 20.2 +/− 0.4 (3) |
| C/EBPa | 10.7 +/− 0.1 (3) | 11.7 +/− 1.2 (3) | 5.8 +/− 1.7 (3) | 8.9 +/− 1.9 (3) | 6.6 +/− 0.6 (3) |
| AFP | 20.9 +/− 1.3 (3) | 19.5 +/− 2.1 (3) | 14.5 +/− 1.6 (4) | 14.1 +/− 0.3 (3) | 11.8 +/− 0.3 (3) |
| TTR | + | + | + | + | + |
| CK19 | 2.3 +/− 0.9 (5) | 1.7 +/− 0.8 (7) | .−1.1 +/− 0.4 (4) | 0.5 +/− 1.1 (7) | 1.2 +/− 0.6 (5) |
| Alb | 21.4 +/− 2.4 (8) | 18.8 +/− 4.4 (9) | 9.8 +/− 1.5 (7) | 6.9 +/− 2.4 (9) | .−2.0 +/− 2.0 (8) |
| CK18 | 1.6 +/− 0.2 (3) | 1.5 +/− 0.6 (3) | 0.5 +/− 0.5 (3) | 0.8 +/− 0.4 (3) | .−0.1 +/− 0.8 (1) |
| AAT | 18.0 +/− 2.7 (6) | 18.0 +/− 4.0 (8) | 10.6 +/− 6.0 (4) | 10.2 +/− 5.9 (8) | 4.8 +/− 3.8 (6) |
| TAT | + | + | + | + | + |
| G6P | 21.7 +/− 0.7 (3) | 15.2 +/− 3.9 (3) | 15.2 +/− 2.7 (3) | 19.2 +/− 2.4 (3) | 16.8 +/− 1.5 (3) |
| Cx32 | 18.6 +/− 1.7 (3) | 19.8 +/− 1.8 (3) | 8.7 +/− 2.8 (3) | 12.5 +/− 3.7 (3) | 10.0 +/− 1.9 (3) |
| PEPCK | + | 4.6 +/− 0.8 (3) | 3.7 +/− 0.3 (2) | 3.9 +/− 0.5 (3) | 6.4 +/− 2.0 (3) |
| CYP1A2 | 19.7 +/− 1.5 (3) | 17.8 +/− 3.6 (3) | 15.6 +/− 3.9 (2) | 22.0 +/− 1.2 (3) | 20.4 +/− 0.1 (3) |
| CYP3A4 | 21.7 +/− 0.7 (3) | 21.7 +/− 0.3 (3) | 21.8 +/− 0.8 (4) | 22.6 +/− 0.4 (3) | 20.7 +/− 0.9 (3) |

TABLE 3b

Gene Expression of hiPS cells
hiPS

| | d 0 | d 6 | d 10 | d 14 | d 20 |
|---|---|---|---|---|---|
| Klf4 Tg | 22.1 (1) | 20.9 (1) | 21.5 (1) | 19.7 (1) | 19.3 (1) |
| Sox2 Tg | 19.6 +/- 3.6 (2) | 18.4 +/- 3.5 (2) | 19.1 +/- 2.8 (2) | 19.7 (1) | 19.3 (1) |
| Oct4 Tg | 21.5 +/- 0.9 (2) | 20.5 +/- 0.6 (2) | 21.3 +/- 0.2 (2) | 19.4 (1) | 19.3 (1) |
| Rex | 8.3 (1) | 13.5 (1) | 12.7 (1) | 18.4 (1) | 17.0 (1) |
| Nanog | 4.8 +/- 0.5 (2) | 8.4 +/- 0.0 (2) | 16.7 +/- 0.9 (2) | 18.1 (1) | 17.6 (1) |
| Sox2 endo | 5.6 +/- 0.4 (2) | 9.0 +/- 0.2 (2) | 16.8 +/- 0.5 (2) | 15.7 (1) | 16.9 (1) |
| Oct4 endo | 8.8 +/- 0.7 (4) | 13.2 +/- 1.4 (4) | 19.5 +/- 1.9 (4) | 17.2 +/- 3.3 (3) | 16.3 +/- 2.2 (3) |
| Mixl1 | 4.8 +/- 0.7 (3) | 4.0 +/- 1.5 (3) | 10.4 +/- 1.9 (3) | 9.0 +/- 2.0 (3) | 9.4 +/- 1.4 (3) |
| Eomes | 4.4 +/- 1.0 (3) | 3.8 +/- 1.5 (3) | 9.0 +/- 1.8 (3) | 8.6 +/- 2.8 (3) | 10.5 +/- 0.6 (3) |
| Brachyury | 5.6 (1) | 6.1 (1) | 7.8 (1) | 8.5 (1) | 7.5 (1) |
| Tm4sf2 | 7.8 +/- 0.7 (3) | 7.0 +/- 0.7 (3) | 9.9 +/- 1.4 (3) | 10.3 +/- 1.5 (3) | 6.9 +/- 0.4 (3) |
| Sox17 | 6.4 +/- 1.2 (3) | 5.5 +/- 1.9 (3) | 7.9 +/- 2.5 (3) | 9.0 +/- 1.4 (3) | 8.3 +/- 1.1 (3) |
| Foxa2 | 9.9 +/- 2.9 (3) | 10.3 +/- 1.3 (3) | 10.6 +/- 1.5 (3) | 12.0 +/- 1.6 (3) | 11.3 +/- 1.7 (3) |
| Cxcr4 | 3.5 +/- 3.1 (3) | 3.2 +/- 2.2 (3) | 7.4 +/- 2.5 (3) | 6.7 +/- 1.6 (3) | 7.2 +/- 1.3 (3) |
| Flk1 | 8.2 +/- 2.2 (3) | 10.5 +/- 2.4 (3) | 13.0 +/- 6.4 (3) | 14.4 +/- 4.6 (3) | 10.1 +/- 3.3 (3) |
| E-cadherin | 4.5 (1) | 4.9 (1) | 3.4 (1) | 4.6 (1) | 2.5 (1) |
| HNF4a | 7.1 +/- 2.0 (3) | 7.4 +/- 0.7 (3) | 6.4 +/- 1.9 (3) | 8.3 +/- 0.3 (3) | 6.4 +/- 0.2 (3) |
| AFP | 19.9 +/- 0.7 (3) | 17.9 +/- 1.3 (3) | 17.3 +/- 0.8 (3) | 18.3 +/- 1.5 (3) | 13.8 +/- 1.8 (3) |
| TTR | + | + | + | + | + |
| CK19 | 1.7 +/- 1.3 (3) | 3.2 +/- 3.0 (3) | 2.9 +/- 3.4 (3) | 3.2 +/- 2.5 (3) | 1.4 +/- 2.6 (3) |
| Alb | 15.9 +/- 2.8 (3) | 19.2 +/- 1.7 (3) | 11.1 +/- 4.7 (3) | 6.5 +/- 2.0 (3) | 0.3 +/- 3.2 (3) |
| CK18 | 0.7 +/- 0.8 (3) | 1.9 +/- 1.0 (3) | 3.7 +/- 2.5 (3) | 3.2 +/- 1.8 (3) | 0.1 +/- 0.7 (3) |
| AAT | 16.9 +/- 2.8 (3) | 19.2 +/- 1.7 (3) | 18.4 +/- 1.6 (3) | 14.8 +/- 0.9 (3) | 9.2 +/- 3.5 (3) |
| TAT | + | + | + | + | + |
| G6P | + | + | + | + | + |
| Cx32 | 16.7 +/- 0.7 (3) | 17.7 +/- 1.0 (3) | 13.7 +/- 2.0 (3) | 15.2 +/- 0.3 (3) | 11.3 +/- 0.7 (3) |
| PEPCK | 5.8 +/- 1.4 (3) | 6.4 +/- 0.5 (3) | 7.3 +/- 0.5 (3) | 6.1 +/- 1.1 (3) | 6.2 +/- 0.5 (3) |
| CYP7A1 | 20.0 +/- 0.9 (2) | 17.2 +/- 0.7 (2) | 17.7 +/- 0.1 (2) | 17.6 +/- 1.2 (2) | 16.6 +/- 1.2 (2) |

Figure 11A:
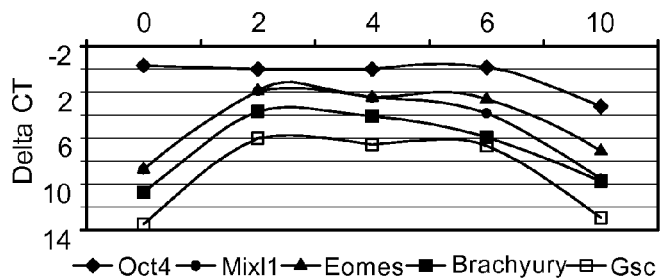
FIG. 11 A-J shows the expression of genes, using RT-qPCR, as well as various markers of differentiation, at different timepoints of differentiation, of the hESC line H9. A=PS phenotype; B=ME/DE phenotype; C=hepatoblast phenotype; D=definitive hepatocyte phenotype; E=concentration of albumin; F=spontaneous production of urea and conversion of $HN_4HCO_3$ to urea; G=glycogen storage at different timepoints of differentiation; H=metabolization of different concentrations of unconjugated bilirubin at different timepoints of differentiation; I=total GST activity at different timepoints of differentiation; and J=expression of coagulation factors Factor V, Factor VII, Protein C, GGCX and VKOR at different timepoints of differentiation.
Figure 11B:
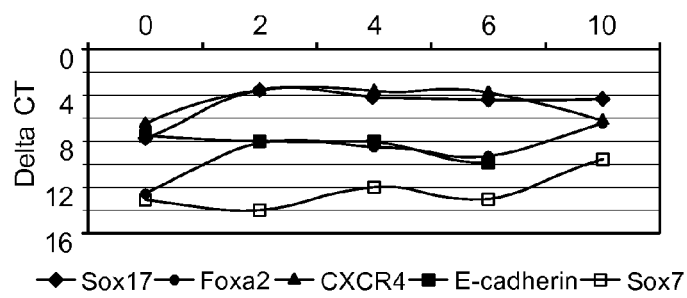
Figure 11C:
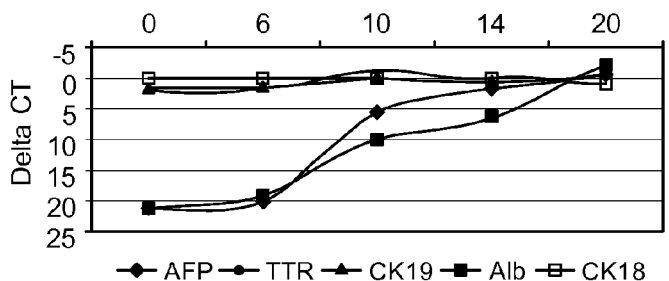
Figure 11D:
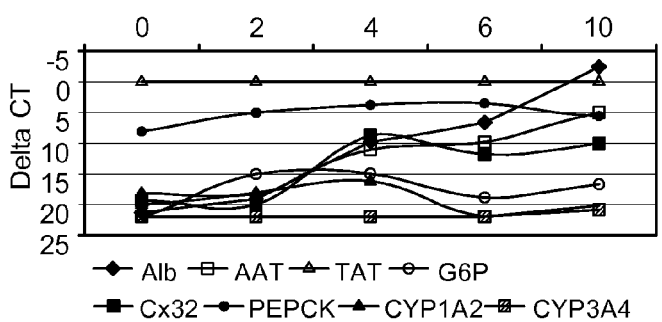
Figure 11E:
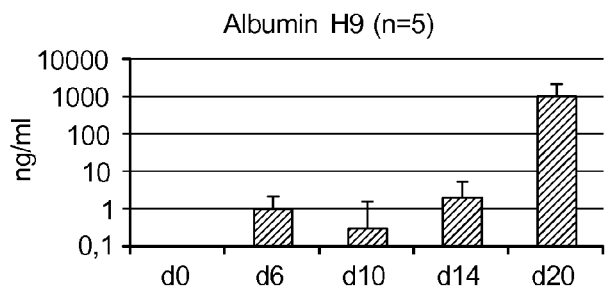
Figure 11F:
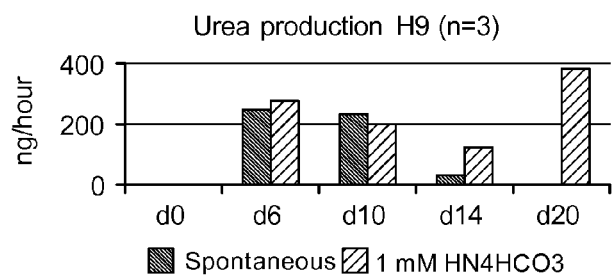
Figure 11G:
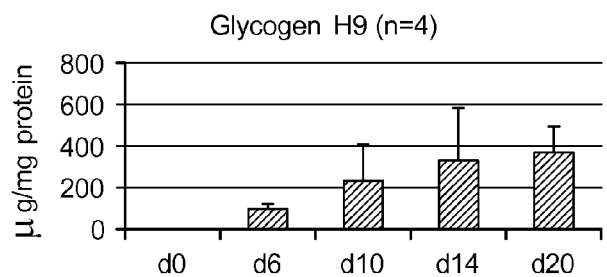
Figure 11H:
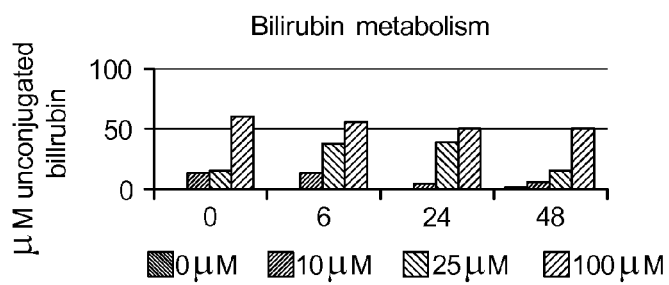
Figure 11I:
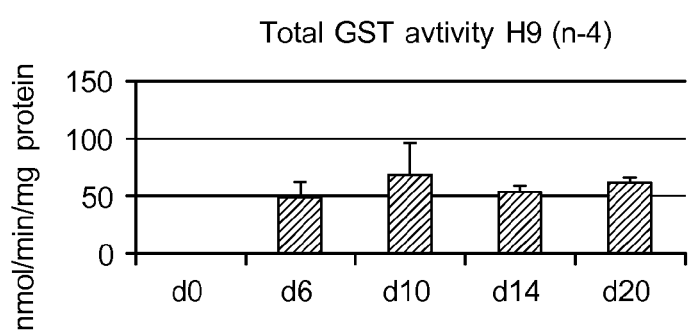
Figure 11J:
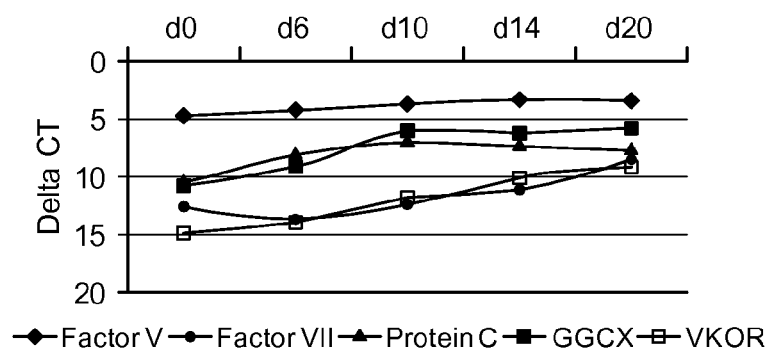
Figure 12:
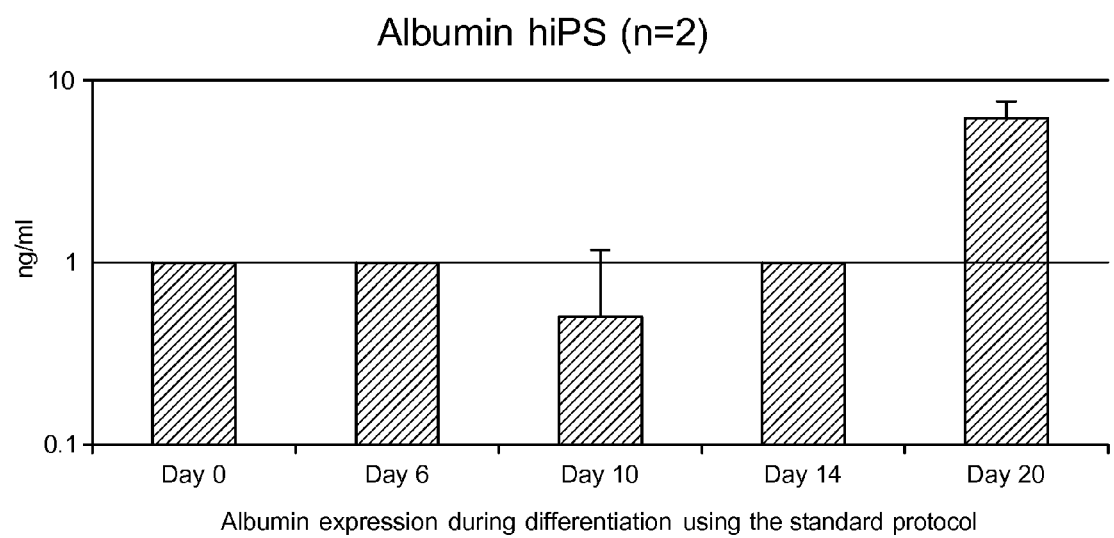
FIG. 12 shows the albumin secreted by hiPS cells during differentiation.

FIG. 11A shows the expression of primitive streak (PS) genes Oct 4, Mix/1, Eomes, brachyury and Gsc at day 0 and after days 2, 4, 6 and 10 of differentiation. FIG. 11B shows the expression of mesoendoderm/definitive endoderm (ME/DE) genes Sox 17, Foxa2, CXCR4, E-cadherin and Sox7 at day 0 and after days 2, 4, 6 10 of differentiation. FIG. 11C shows the expression of hepatoblast genes AFP, TTR, CK19, A1b and CK18 at day 0 and after days 6, 10, 14 and 20 of differentiation. FIG. 11D shows the expression of definitive hepatocyte genes Alb, AAT, TAT, G6P, Cx32, PEPCK, CYP1A2 and CYP3A4 at day 0 and after days 6, 10, 14 and 20 of differentiation. FIG. 11E shows the concentration of albumin secreted by the H9 cell cultures. FIG. 11F shows the spontaneous production of urea and the conversion of $HN_4HCO_3$ (1 mM) to urea of the H9 cells. FIG. 11G shows glycogen storage of the H9 cells at day 0 and after days 6, 10, 14 and 20 of differentiation. FIG. 11H shows the metabolization of different concentrations of unconjugated bilirubin at day 0 and after days 6, 10, 14 and 20 of differentiation. FIG. 11I shows the total GST activity at day 0 and after days 6, 10, 14 and 20 of differentiation. FIG. 11J shows the expression of coagulation factors Factor V, Factor VII, Protein C, GGCX and VKOR at day 0 and after days 6, 10, 14 and 20 of differentiation. FIG. 12 shows the concentration of albumin secreted by hiPS cells.

While the invention has been particularly shown and described with reference to preferred embodiments thereof, it will be understood by those skilled in the art that various alterations in form and detail may be made therein without departing from the spirit and scope of the invention, as defined by the appended claims.

All references cited herein are incorporated by reference for the teachings referred to in citing these references.

What is claimed is:

1. A method for inducing cells to differentiate into cells that express a hepatocyte phenotype, said method comprising the steps of:
   (a) culturing either mouse or human embryonic stem (ES) cells, mouse or human induced pluripotent stem (iPS) cells or mouse, rat, or human multipotent adult progenitor cells characterized in that the multipotent adult progenitor cells can differentiate into at least one cell type of each of the endodermal, ectodermal, and mesodermal embryonic lineages but are not embryonic germ cells, embryonic stem cells, or germ cells, with about 5 ng/ml to about 500 ng/ml Wnt3a and about 10 ng/ml to about 1,000 ng/ml ActivinA, to obtain cells that express a definitive endoderm phenotype,
   (b) then culturing the cells produced in step (a) with about 1 ng/ml to about 100 ng/ml bFGF and about 5 ng/ml to about 5 ng/ml to about 50 ng/ml BMP4, to obtain cells that express a liver committed endodermal phenotype,
   (c) then culturing the cells produced in step (b) with about 5 ng/ml to about 500 ng/ml aFGF, about 1 ng/ml to about 100 ng/ml FGF4 and about 2.5 ng/ml to about 250 ng/ml FGF8b, to obtain cells that express a hepatoblast phenotype, and (d) then culturing the cells produced in step (c) with about 2 ng/ml to about 200 ng/ml HGF and about 10 ng/ml to about 1,000 ng/ml Follistatin, to obtain cells that express a hepatocyte phenotype.

2. The method of claim 1, wherein the cells are cultured in step (a) with about 50 ng/ml Wnt3a and about 100 ng/ml ActivinA.

3. The method of claim 1, wherein the cells are cultured in step (b) with about 10 ng/ml bFGF and about 50 ng/ml BMP4.

4. The method of claim 1, wherein the cells are cultured in step (c) with about 50 ng/ml aFGF, about 10 ng/ml FGF4 and about 25 ng/ml FGF8b.

5. The method of claim 1, wherein the cells are cultured in step (d) with about 20 ng/ml HGF and about 100 ng/ml Follistatin.

6. The method of claim 1, wherein the cells are cultured at one or more steps in a medium containing a serum concentration ranging from 0% to about 2%.

7. The method of claim 1, wherein the cells are cultured at one or more steps in a medium containing about $10^{-5}$ M to about $10^{-10}$ M dexamethasone.

8. The method of claim 1, wherein the cells are cultured at one or more steps for at least four days.

9. The method of claim 1, wherein the cells in step (a) are cultured for about six days, the cells in step (b) are cultured for about four days, the cells in step (c) are cultured for about four days, and the cells in step (d) are cultured for about seven days.

10. The method of any of claims 1-9, wherein the multipotent adult progenitor cells are derived from bone marrow.

* * * * *